US009511133B2

(12) United States Patent
Holmgren et al.

(10) Patent No.: US 9,511,133 B2
(45) Date of Patent: Dec. 6, 2016

(54) VACCINE AGAINST CHOLERA AND ENTEROTOXIGENIC E. COLI (ETEC) DIARRHEA

(75) Inventors: Jan Holmgren, Västra Frölunda (SE); Michael Lebens, Hökerum (SE)

(73) Assignee: MSD Wellcome Trust Hilleman Laboratories Pvt Ltd., New Delhi (IN)

( * ) Notice: Subject to any disclaimer, the term of this patent is extended or adjusted under 35 U.S.C. 154(b) by 159 days.

(21) Appl. No.: 13/496,183

(22) PCT Filed: Sep. 16, 2010

(86) PCT No.: PCT/SE2010/050996
§ 371 (c)(1),
(2), (4) Date: Jul. 18, 2012

(87) PCT Pub. No.: WO2011/034495
PCT Pub. Date: Apr. 24, 2011

(65) Prior Publication Data
US 2012/0276146 A1 Nov. 1, 2012

Related U.S. Application Data

(60) Provisional application No. 61/272,351, filed on Sep. 16, 2009.

(51) Int. Cl.
*A61K 39/106* (2006.01)
*A61K 39/02* (2006.01)
*A61K 39/00* (2006.01)

(52) U.S. Cl.
CPC ....... *A61K 39/107* (2013.01); *A61K 2039/521* (2013.01); *A61K 2039/523* (2013.01)

(58) Field of Classification Search
CPC .................................................. A61K 39/107
See application file for complete search history.

(56) References Cited

U.S. PATENT DOCUMENTS

| 5,330,753 | A | 7/1994 | Mekalanos et al. |
| 5,882,653 | A | 3/1999 | Kaper et al. |
| 5,942,242 | A | 8/1999 | Mizushima et al. |
| 6,203,799 | B1 | 3/2001 | Mekalanos et al. |
| 7,270,961 | B2 | 9/2007 | Chang et al. |
| 2006/0099229 | A1 | 5/2006 | Ravichandran et al. |

FOREIGN PATENT DOCUMENTS

| WO | 94/01533 A1 | 1/1994 |
| WO | 00/67784 A1 | 11/2000 |
| WO | 2009/049013 A2 | 4/2009 |

OTHER PUBLICATIONS

Office Action received for Chinese Patent Application No. 201080041458.1, mailed on Jun. 28, 2013, 25 pages (14 pages of English Translation and 11 pages.).
International Preliminary Report on Patentability received for PCT Patent Application No. PCT/SE2010/050996, mailed on Mar. 29, 2012, 11 pages.
GenBank, "Vibrio Cholerae O1 Biovar Eltor WbeT (WbeT) Gene, Partial Cds", Accession No. D0401028.1, Sep. 6, 2006, 1 page.
GenBank, "Vibrio Cholerae Strain 2132 WbeT Gene, Partial Cds", Accession No. FJ619106.1, Mar. 14, 2012, 1 page.
Grinter, Nigel J., "A Broad-Host-Range Cloning Vector Transposable to Various Replicons", Elsevier Biomedical Press, Gene, vol. 21, 1983, pp. 133-143.
Tobias et al., "Construction and Expression of Immunogenic Hybrid Enterotoxigenic *Escherichia Coli* CFA/I and CS2 Colonization Fimbriae for Use in Vaccines", Applied Microbiology and Biotechnology, vol. 87, 2010, pp. 1355-1365.
Tobias et al., "Over-Expression of Major Colonization Factors of Enterotoxigenic *Escherichia coli*, Alone or Together, on Non-Toxigenic *E. coli* Bacteria", Vaccine, vol. 28, 2010, pp. 6977-6984.
Office Action received for Australian Patent Application No. 2010296065, issued on Oct. 21, 2013, 3 page.
Extended European Search Report and Search Opinion received for Patent Application No. 10817520.9, mailed on Jan. 7, 2013, 15 pages.
International Search Report and Written Opinion received for PCT Patent Application No. PCT/SE2010/050996, mailed on Nov. 30, 2010, 17 pages.
Anh et al., "Safety and Immunogenicity of a Reformulated Vietnamese Bivalent Killed, Whole-Cell, Oral Cholera Vaccine in Adults", Vaccine, vol. 25, 2007, pp. 1149-1155.
Chiang et al., "Construction of a Vibrio cholerae Vaccine Candidate Using Transposon Delivery and Flp Recombinase-Mediated Excision", Infection and Immunity, vol. 68, No. 11, Nov. 2000, pp. 6391-6397.
Clemens et al., "Field Trial of Oral Cholera Vaccines in Bangladesh: Evaluation of Anti-Bacterial and Anti-Toxic Breast-Milk Immunity in Response to Ingestion of the Vaccines", Vaccine, vol. 8, Oct. 1990, pp. 469-472.
Dukoral, "Oral, Inactivated Travellers" Diarrhea and Cholera Vaccine, Product Monograph, ATCC Code: JO7AE01, Nov. 2007, pp. 1-27.
Dutta et al., "Spread of Cholera with Newer Clones of Vibrio cholerae O1 El Tor, Serotype Inaba, in India", Journal of Clinical Microbiology, vol. 44, No. 9, Sep. 2006, pp. 3391-3393.
Holmgren et al., "An Oral B Subunit: Whole Cell Vaccine against Cholera", Vaccine, vol. 10, No. 13, 1992, pp. 911-914.
Holmgren et al., "New Cholera Vaccines", Vaccine, vol. 7, Apr. 1989, pp. 94-96.
Jertborn et al., "Safety and Immunogenicity of an Oral Recombinant Cholera B Subunit—Whole Cell Vaccine in Swedish Volunteers", Vaccine, vol. 10, No. 2, 1992, pp. 130-132.

(Continued)

*Primary Examiner* — Patricia Duffy
(74) *Attorney, Agent, or Firm* — Morrison & Foerster LLP

(57) ABSTRACT

A vaccine against cholera and/or ETEC is provided, comprising a *Vibrio cholerae* O1 cell, characterized in that said cell comprises O1 antigens of both Ogawa and Inaba serotypes. Genetically modified *Vibrio cholerae* O1 cells for use in such vaccines, DNA-constructs for the modification, uses for the vaccine and methods of making a vaccine are also provided.

10 Claims, No Drawings

(56) References Cited

OTHER PUBLICATIONS

Kanungo et al., "Immune Responses Following One and Two Doses of the Reformulated, Bivalent, Killed, Whole-Cell, Oral Cholera Vaccine among Adults and Children in Kolkata, India: A Randomized, Placebo-Controlled Trial", Vaccine, vol. 27, 2009, pp. 6887-6893.

Lebens et al., "Construction of Novel Vaccine Strains of Vibria Cholerae Co-Expressing the Inaba and Ogawa serotype antigens", Vaccine, vol. 29, 2011, pp. 7505-7513.

Lycke et al., "Strong Biotype and Serotype Cross-Protective Antibacterial and Antitoxic Immunity in Rabbits after Cholera Infection", Microbial Pathogenesis, vol. 1, 1986, pp. 361-371.

Manning et al., "Molecular Cloning and Expression in *Escherichia coli* K-12 of the O antigens of the Inaba and Ogawa Serotypes of the Vibrio Cholerae O1 Lipopolysaccharides and their Potential for Vaccine Development", Infection and Immunity, vol. 53, No. 2, Aug. 1986, pp. 272-277.

Nygren et al., "Establishment of an Adult Mouse Model for Direct Evaluation of the Efficacy of Vaccines against Vibrio cholerae", Infection and Immunity, vol. 77, No. 8, Aug. 2009, pp. 3475-3484.

Rijpkema et al., "Assessing Clonality of Vibrio Cholerae Inaba Isolates by Characterization of Nonsense Mutations in wbeT", Journal of Medical Microbiology, vol. 53, 2004, pp. 1105-1107.

Sanchez et al., "Virulence Factors, Pathogenesis and Vaccine Protection in Cholera and Etec Diarrhea", Current Opinion in Immunology, vol. 17, 2005, pp. 388-398.

Shamsuzzaman et al., "Robust Gut associated Vaccine-Specific Antibody-Secreting Cell Responses are detected at the Mucosal Surface of Bangladeshi Subjects after Immunization with an Oral Killed Bivalent V. Cholerae O1/O139 Whole Cell Cholera Vaccine: Comparison with Other Mucosal and Systemic Responses", Vaccine, vol. 27, 2009, pp. 1386-1392.

Stroeher et al., "Serotype Conversion in Vibrio Cholerae O1", Proceedings of the National Academy of Sciences, USA, Microbiology, vol. 89, Apr. 1992, pp. 2566-2570.

Taylor et al., "Evaluation of a Bivalent (CVD 103-HgR/CVD 111) Live Oral Cholera Vaccine in Adult Volunteers from the United States and Peru", Infection and Immunity, vol. 65, No. 9, Sep. 1997, pp. 3852-3856.

Taylor et al., "Expanded Safety and Immunogenicity of a Bivalent, Oral, Attenuated Cholera Vaccine, CVD 103-HgR Plus CVD 111, in United States Military Personnel Stationed in Panama", Infection and Immunity, vol. 67, No. 4, Apr. 1999, pp. 2030-2034.

Tobias et al., "Construction of Non-Toxic *Escherichia coli* and Vibrio Cholerae Strains Expressing High and Immunogenic Levels of Enterotoxigenic *E. coli* Colonization Factor I Fimbriae", Vaccine, vol. 26, 2008, pp. 743-752.

Office Action received for Chinese Patent Application No. 201080041458.1, issued on Feb. 7, 2014, 9 pages (6 pages of English Translation and 3 pages).

Ali et al., "Natural Cholera Infection-Derived Immunity in an Endemic Setting," JID, Sep. 2011, pp. 912-918, vol. 204.

Clemens et al., "New-generation vaccines against cholera," Nature Reviews, Gastroenterology & Hepatology, Dec. 2011, pp. 701-710, vol. 8.

Feely et al., "Field Trials of Cholera Vaccine," Cholera and Related Diarrheas, 43rd Nobel Symp., Stockholm 1978, Karger, 1980, pp. 204-210.

Gustafsson et al., "Immunological Characterization of *Vibrio cholerae* 0:1 Lipopolysaccharide, O-Side Chain, and Core with Monoclonal Antibodies," Infection and Immunity, Aug. 1985, pp. 275-280, vol. 49, No. 2.

Holmgren et al., "Vaccines against mucosal infections," Current Opinion in Immunology, 2012, pp. 343-353, vol. 24.

Karlsson et al., "Development of Stable *Vibrio cholerae* O1 Hikojima Type Vaccine Strains Co-Expressing the Inaba and Ogawa Lipopolysaccharide Antigens," Plos One, Nov. 2014, pp. 1-13, vol. 9, No. 11.

Levine, "Immunity to Cholera as Evaluated in Volunteers," Cholera and Related Diarrheas, 43rd Nobel Symp., Stockholm 1978, Karger, 1980, pp. 195-203.

Longini, Jr. et al., "Epidemic and Endemic Cholera Trends over a 33-Year Period in Bangladesh," JID, Jul. 2002, pp. 246-251, vol. 186.

Mannnig et al., "Molecular Basis for O-Antigen Biosynthesis in *Vibrio cholerae* O1: Ogawa-Inaba Switching," *Vibrio cholerae* and Cholera: Molecular to Global Perspectives, 1994, pp. 77-94.

Mosley et al., "Report of the 1966-67 Cholera Vaccine Field Trial in Rural East Pakistan," 1969, Bull. Wld Hlth Org., 1969, pp. 177-185, vol. 40.

Mosley et al., "Field trials of monovalent Ogawa and Inaba cholera vaccines in rural Bangladesh-three years of observation," Bull. Wld Hlth Org., 1973, pp. 381-387, vol. 49.

Svennerholm, "The Nature of Protective Immunity in Cholera," Cholera and Related Diarrheas, 43rd Nobel Symp., Stockholm 1978, Karger, 1980, pp. 171-184.

VACCINE AGAINST CHOLERA AND ENTEROTOXIGENIC E. COLI (ETEC) DIARRHEA

CROSS REFERENCE TO RELATED APPLICATIONS

This is a U.S. National Phase patent application of PCT/SE2010/050996, filed Sep. 16, 2010, which claims priority to the U.S. Provisional Patent Application No. 61/272,351, filed Sep. 16, 2009, each of which is hereby incorporated by reference in the present disclosure in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 616562008000SeqListing.txt, date recorded: Feb. 27, 2012, size: 32 KB).

TECHNICAL FIELD THE INVENTION

The present invention relates to the field of vaccines, in particular vaccines against cholera and enterotoxigenic *E. coli* (ETEC) diarrhea.

BACKGROUND TO THE INVENTION

Cholera remains a major health problem in large parts of the world. This is also true for ETEC, which is the main cause of diarrheal disease in developing countries as well as in travelers to these countries. In many developing countries effective water and sanitary measures for control of cholera and other enteric infections are currently impossible, and in this context, vaccines have an important role to play. In order to do so however, they need to be effective, readily accessible and above all cheap. There is also a medical need and a very substantial commercial market for use of cholera and especially ETEC vaccines in travelers.

One approach has been the development of oral killed whole cell vaccines. The oral vaccine sold under the trademark, DUKORAL™ is an oral, monovalent inactivated vaccine containing killed whole cells of *V. cholerae* O1 plus additional recombinant cholera toxin B subunit with demonstrated up to 90% efficacy against cholera and also a significant efficacy against Enterotoxigenic *Escherichia coli* (ETEC)-induced diarrhea. It comprises 3 different *V. cholerae* strains in four different formulations (two heat-killed and two formalin-killed) and in addition recombinantly produced cholera toxin B subunit (rCTB). The rCTB component contributes significantly to the efficacy against cholera and is solely responsible for the observed protection against ETEC diarrhea due to its ability to induce cross-neutralizing antibodies against the cholera toxin (CT)-like *E. coli* heat-labile toxin (LT). However, rCTB is acid-labile and thus the vaccine (which needs to be given in two doses) must be administered with a bicarbonate buffer.

Despite DUKORAL™, which is an oral, monovalent inactivated vaccine containing killed whole cells of *V. cholerae* O1 plus additional recombinant cholera toxin B subunit, being the only internationally licensed OCV, copies of this vaccine with or without the CTB component are currently being marketed in developing countries—Vietnam, India and China. The OCV made in Vietnam and India (which lacks the CTB component) contains the same 4 bacterial components as in the oral vaccine sold under the trademark, DUKORAL™, which is an oral, monovalent inactivated vaccine containing killed whole cells of *V. cholerae* O1 plus additional recombinant cholera toxin B subunit, plus a fifth formalin-killed *V. cholerae* strain of serogroup O139.

Protective immunity against cholera elicited by OCVs is mainly if not exclusively based on mucosal production of antibodies against cell wall lipopolysaccharide O1 (O1 LPS) and for the CTB-containing the oral vaccine sold under the trademark, DUKORAL™, which is an oral, monovalent inactivated vaccine containing killed whole cells of *V. cholerae* O1 plus additional recombinant cholera toxin B subunit, also antitoxin antibodies in the intestine.

From the above it is evident that the present state of the art for production of cholera/ETEC vaccine is far from simple, and although already effective, a real contribution to making a cholera vaccine more accessible would be to rationalize the composition of the formulation at several levels.

The necessity to include several different *Vibrio cholerae* strains in killed whole cell vaccines arises from the need to represent several different antigenic variants of *Vibrio cholerae* in the vaccine. All protective strains in the currently used vaccines are of the O1 serogroup which until 1993 was the only one of more than 200 identified serogroups known to cause epidemic cholera and is still the dominant serogroup. However, the O1 serogroup has two variants called the Ogawa and Inaba serotypes that differ in the methylation of the terminal sugar of the O-antigen of the surface lipopolysaccharide (LPS). Serotype switching is known to occur in which the Ogawa serotype organism can give rise to Inaba organisms. The reverse switch however is rare.

Although immunization with especially Inaba but also Ogawa serotype can give rise to antibodies cross-reacting with the other serotypes it also gives rise to serotype specific antibodies that contribute significantly to protection. Thus, an effective vaccine should induce not only cross reactive but also serotype-specific antibodies against both Inaba and Ogawa serotype variants.

The serotype switch is known to be related to a mutation in a single gene (wbeT). Any mutation that inactivates this gene results in a switch from the Ogawa to the Inaba serotype. Mutations that can reverse such an event are predictably much more uncommon although a switch from the Inaba to the Ogawa serotype can easily be achieved by provision of the relevant gene in trans. The gene involved (wbeT, also denoted rfbT) encodes a methyl transferase that methylates the terminal perosamine residue in the O-antigen polysaccharide repeating unit. Mutations in this gene that lead to the Inaba serotype are almost invariably insertions, deletions or base changes that introduce a nonsense codon.

A third O1 variant known as Hikojima has also been documented to occur in the wild. Hikojima is characterized by that it expresses both the Ogawa and Inaba determinants on its surface and agglutinates with antisera specific for both types. The Hikojima phenotype is extremely rare and is considered in the literature to be an unstable transitional form.

With this in mind the inventors have set out to engineer a single vaccine strain of *V. cholerae* that would effectively replace the three currently used strains.

Thus, it is an object of the invention to provide an efficient vaccine against cholera and/or ETEC diarrhea, with simplified formulation and with lower productions costs and that also ideally produces protective immunity after single administration.

SUMMARY OF THE INVENTION

The present invention describes the construction, method of manufacture, formulation and medical-preventive use of a novel cholera and/or ETEC vaccine.

Throughout this text, in line with established scientific practice, the designation "wbeT" (in italics) denotes the gene, whereas the designation "WbeT" (in italics) denotes a protein coded for by a wbeT gene.

In a first aspect, a vaccine comprising a *Vibrio cholerae* O1 cell, characterized in that said cell comprises O1 antigens of both Ogawa and Inaba serotypes is provided.

The vaccine may comprise multiple *Vibrio cholerae* O1 cells that comprise O1 antigens of both Ogawa and Inaba serotypes, and wherein on average, 10-90% of the O1 antigens of said cells are of the Ogawa-serotype.

Preferably, 10-90% of the O1 antigen expressed by the cells is of the Ogawa-serotype. More preferably, 10-70% of the O1 antigen expressed by the cells is of the Ogawa-serotype. Yet more preferably, 10-50% of the O1 antigen expressed by the cells is of the Ogawa-serotype. Still more preferably, 10-40% of the O1 antigen expressed by the cells is of the Ogawa-serotype. Most preferably, 10-30% of the O1 antigen expressed by the cells is of the Ogawa-serotype.

The cell of the vaccine may further comprise one or more ETEC colonization factor (CF) protein(s), such as CFA/I, CS2 or CS5, wherein said CF protein(s) is/are expressed either as single, double or hybrid fimbriae.

Preferably, said vaccine does not contain any further immunogically active whole cells in addition to *Vibrio cholerae* O1 cells that comprise O1 antigens of both Ogawa and Inaba serotypes.

Preferably, the vaccine is for oral administration. Preferably, the cell in the vaccine is formalin-inactivated.

Preferably, the cell is a genetically modified cell, preferably a genetically modified cell according the seventh or eighth aspects of the invention (see below).

In a second aspect a vaccine according to the first aspect is provided, for use in preventive immunization, preferably for use in preventive immunization against cholera and/or enterotoxigenic *Escherichia coli*-infection (ETEC).

In a third aspect, a method for inducing preventive immunity is provided, comprising administering a vaccine according to the first aspect to a subject to be immunized. Preferably, the preventive immunity is against cholera and/or enterotoxigenic *Escherichia coli*-infection (ETEC). Also preferably, the administration is done orally.

In a fourth aspect, a DNA-construct is provided, comprising DNA coding for a WbeT-protein having at least 70% sequence identity to SEQ ID NO: 6 (more preferably at least 80% identity, even more preferably at least 90% identity, yet more preferably at least 95% identity and most preferably at least 99% identity) operatively coupled to a promoter suitable for inducing protein expression in a *Vibrio cholerae* O1 host cell, characterized in that the coded WbeT-protein comprises sequence modifications in relation to SEQ ID NO: 6 that reduce the enzymatic activity of the coded protein relative to the enzymatic activity of a protein with a sequence identical to SEQ ID NO: 6.

Preferably, the sequence modifications comprise a substitution of the serine residue in position 158 of SEQ ID NO: 6, more preferably a substitution of the serine residue in position 158 of SEQ ID NO: 6 to glycine, proline, threonine, phenylalanine or tryptophan.

In a fifth aspect, a DNA-construct is provided, comprising DNA coding for a WbeT-protein having at least 70% sequence identity to SEQ ID NO: 6 (more preferably at least 80% identity, even more preferably at least 90% identity, yet more preferably at least 95% identity and most preferably at least 99% identity) operatively coupled to a promoter suitable for inducing protein expression in a *Vibrio cholerae* O1 host cell, characterized in that the promoter is suitable for inducing the expression of the coded WbeT-protein in a *Vibrio cholerae* O1 host cell initially of Inaba phenotype (i.e. host cell which is Inaba prior to transformation by the DNA construct) to such level of transgenic WbeT protein expression as to allow simultaneous expression of both Inaba and Ogawa antigens by the host cell.

Preferably, the promoter of the above aspects is an inducible promoter, such as a tac or lac promoter.

Preferably, the DNA construct of the above aspects is a plasmid vector capable of replication in a host cell or a vector capable of chromosomal integration in a host cell.

Preferably, the DNA-construct according to the above aspects further comprises a selectable marker, more preferably a positive selectable marker such as antibiotic resistance gene or a metabolic selectable marker.

In a sixth aspect, a DNA construct for homologous recombination in a *Vibrio Cholerae* O1 host is provided, characterized in that the construct is adapted to modifying the endogenous wbeT gene of the host by means of homologous recombination. Preferably, the DNA-construct according to the sixth aspect further comprises a selectable marker, more preferably a positive selectable marker such as antibiotic resistance gene or a metabolic selectable marker.

In a seventh aspect, a *Vibrio cholerae* O1 cell simultaneously expressing both Inaba and Ogawa antigens is provided, characterized in that
 a. the endogenous wbeT-gene of the host cell or the protein coded thereof is inactive;
 b. the cell comprises a recombinant DNA-construct inducing expression of WbeT enzyme activity; and wherein
 c. the level of transgenic WbeT enzyme activity is such that the cell simultaneously expresses Inaba and Ogawa antigens.

Preferably, the recombinant DNA-construct of the above aspects is a DNA construct according to the fourth to fifth aspects.

In an eighth aspect, a *Vibrio cholerae* O1 cell simultaneously expressing both Inaba and Ogawa antigens is provided, characterized in that
 a. the cell comprises an endogenous wbeT-gene; and
 b. the cell comprises a recombinant DNA-construct capable of modulating the expression level of endogenous wbeT gene or the enzymatic activity of the product thereof; and wherein
 c. the modulated level of WbeT enzyme activity is such that the cell simultaneously expresses Inaba and Ogawa antigens.

Preferably, the recombinant DNA-construct of the above aspect is a DNA construct according to the sixth aspect.

Preferably, 10-90% of the O1 antigen expressed by the cell of the above aspects is of the Ogawa-serotype. More preferably, 10-70% of the O1 antigen expressed by the cell of the above aspects is of the Ogawa-serotype. Yet more preferably, 10-50% of the O1 antigen expressed by the cell of the above aspects is of the Ogawa-serotype. Still more preferably, 10-40% of the O1 antigen expressed by the cell of the above aspects is of the Ogawa-serotype. Most preferably, 10-30% of the O1 antigen expressed by the cell of the above aspects is of the Ogawa-serotype.

Preferably, the cell of the above aspects further expresses one or more ETEC colonization factor (CF) protein(s), such as CFA/I, CS2 or CS5, wherein said CF protein(s) is/are expressed either as single, double or hybrid fimbriae.

In a ninth aspect, a method for manufacturing a vaccine is provided, comprising the steps of:
providing a *Vibrio cholerae* O1 cell comprising O1 antigens of both Ogawa and Inaba serotypes; and killing said cell.

Preferably, the killing is performed by formalin-treatment or by heat-treatment.

Preferably, the cell is a cell according to the seventh or the eighth aspects.

In a tenth aspect, the invention also relates to a kit for use in vaccination formulated as a one-unit composition, whereby the composition is presented in one part of the kit and instructions for use in another part.

DETAILED DESCRIPTION OF THE INVENTION

Vaccine Comprising Cells with O1 Antigens of Both Ogawa and Inaba Serotypes

Although *V. cholerae* of serogroup 0139 can also cause cholera, >98% of all cholera worldwide is caused by *V. cholerae* O1. The O1 serogroup has two subtypes/serotypes—Ogawa and Inaba. Serotype switching from the Ogawa to the Inaba subtype occurs at a relatively high frequency whereas the reciprocal conversion is rare. The basis of the serotype switch is a mutation in the LPS synthetic pathway that leads to change in the structure of the O1 antigen. An effective vaccine need to include both Ogawa and Inaba strains in its composition since their LPS are serologically distinct with both shared and distinct epitopes contributing to protection.

A vaccine comprising *Vibrio cholerae* O1 cells expressing O1 antigens of both Ogawa and Inaba serotypes is disclosed, and has the advantage of simplifying production because it obviates the need to use distinct cells for each of the phenotypes in the manufacture of the vaccine. By enabling the use of single type of cell, the manufacture of the vaccine is also simplified, since only one type of inactivation treatment is needed.

Immunization with vaccine of the invention based on single *V. cholerae* strain that express different amounts of both Ogawa and Inaba serotypes gives rise to cross-reactive as well as type-specific antibodies to both Ogawa and Inaba antigens (see example 1).

It is preferable that on average, 10-90% of the O1 antigens of the cells are of the Ogawa-serotype. The Inaba-antigen is preferably present in a higher amount (meaning more than 50%) than the Ogawa-antigen, as the Inaba-antigen can elicit a certain level of cross-serotype protection against Ogawa, whereas Ogawa-antigen can only elicit protection against itself.

The efficacy of the vaccine against ETEC may further be improved by incorporation of the feature that the cells further express one or more ETEC colonization factor (CF) protein(s), such as CFA/I, CS2 or CS5, wherein said CF protein(s) is/are expressed either as single, double or hydrid fimbriae (see below for details).

It is preferable, that the above vaccine does not contain any further immunogically active whole cells in addition to *Vibrio cholerae* O1 cells that comprise O1 antigens of both Ogawa and Inaba serotypes. However, the above vaccine may further comprise recombinant CTB in a manner similar to the oral vaccine sold under the trademark, DUKORAL™, which is an oral, monovalent inactivated vaccine containing killed whole cells of *V. cholerae* O1 plus additional recombinant cholera toxin B subunit.

The vaccine is preferably for oral administration, but may also be administered by injection. Preferably, the vaccine comprises *Vibrio cholerae* O1 cells that comprise O1 antigens of both Ogawa and Inaba serotypes that are formalin-inactivated.

Preferably, the vaccine comprises genetically modified *Vibrio cholerae* O1 cells, preferably such genetically modified *Vibrio cholerae* O1 cells as described below.

The vaccine of the invention may be a vaccine composition comprising one or more pharmaceutically acceptable, excipients, carriers, diluents and adjuvants.

The formulation of vaccine compositions according to the invention is well known to persons skilled in the art. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically active substances is well known in the art, and is described, by way of example, in Remington's Pharmaceutical Sciences, 18th Edition, Mack Publishing Company, Pennsylvania, USA. Except insofar as any conventional media or agent is incompatible with the active ingredient, use thereof in the pharmaceutical compositions of the present invention is contemplated. Supplementary active ingredients can also be incorporated into the compositions.

The vaccine composition for oral use may preferably comprise $10^8$-$10^{14}$ cells/ml, more preferably $10^{10}$-$10^{12}$ cell per ml, and most preferably about $10^{11}$ cells/ml.

The vaccine composition for oral use may be formulated as a foodstuff, beverage or a feed supplement (when for use in immunizing animals).

The vaccine composition may comprise an adjuvant known in the art, or may lack any adjuvants.

Use of the Vaccine

The present invention discloses use of the above vaccine in preventive immunization, preferably against cholera and/or enterotoxic *Escherichia coli*-infection (ETEC).

Preferably, the vaccine is administered orally or sublingually.

The present invention also discloses a method for inducing preventive immunity, comprising administering a vaccine according to the above to a subject to be immunized. Preferably, the preventive immunity is against cholera and/or enterotoxic *Escherichia coli*-infection (ETEC). Preferably, the administration is done orally or sublingually. The administration may also be done by injection.

The vaccine is preferably used to immunize humans and other mammals, such as pets (cats, dogs and the like) or farm animals (such as cows, horses, sheep, goats, pigs and the like).

Preferably, the vaccine is administered orally at $10^8$-$10^{14}$ cells per dose, more preferably $10^{10}$-$10^{12}$ cells per dose, and most preferably about $10^{11}$ cells per dose.

The immunization protocol may consist of a single administration or may comprise two or more administrations. In a preferred embodiment, the initial immunization protocol to induce protective immunity comprises a first administration and a second administration, separated in time by at least 7 days but by no more than about 2 months. After the initial immunization protocol, protective immunity may be maintained as long as desired by booster administrations occurring with less than 3 year intervals, preferably less than 2 year intervals. It is may be preferable that a booster administration does not take place before at least 1 year has elapsed from the first administration.

Method of Manufacture for a Vaccine

A method for manufacturing a vaccine is disclosed, comprising the steps of:
a. providing a *Vibrio cholerae* O1 cell comprising O1 antigens of both Ogawa and Inaba serotypes; and
b. killing said cell, such as by formalin treatment or by heat treatment.

Preferably, the killing is performed by formalin-treatment. Preferably the cell is a genetically modified cell, preferably such as described below.

Besides having the advantage enabling the use of a single inactivation (killing) method, the vaccine may be manufactured using standard protocols known e.g. from the manufacture of the oral vaccine sold under the trademark, DUKORAL™, which is an oral, monovalent inactivated vaccine containing killed whole cells of *V. cholerae* O1 plus additional recombinant cholera toxin B subunit.

Genetically Modified Cells Useful for Vaccine Manufacture and DNA Constructs for Obtaining Such Cells The *Vibrio cholerae* cells comprising O1 antigens of both Ogawa and Inaba serotypes comprised in the vaccine could in principle be obtained from a naturally occurring strain having a Hikojima phenotype. However, to the best knowledge of the inventors such strains are very rare and no such strains are presently available to the public. In the literature, such natural strains have also been described as unstable, which renders them less promising for industrial production of vaccines.

Thus, the inventors have derived *V. cholerae* cells that express O1 antigens of both Ogawa and Inaba serotypes by way of genetic engineering and have obtained novel strains with stable Hikojima phenotype. Cells derived in this manner also have the advantage that any desired strain (such as a known and well-characterized vaccine strain) can be used as a starting point, substantially simplifying the production and streamlining the experiments needed for GMP production and regulatory approval.

The inventors demonstrate herein that the key parameter for obtaining the desired Hikojima phenotype is to obtain a suitable level of WbeT enzyme activity. By suitable in this context is meant that the WbeT enzyme activity level of the cell is not so low that the cells have an essentially pure Inaba phenotype and not so high that the cells have an essentially pure Ogawa phenotype.

In the context of the present invention, it is preferable that 10-90% of the O1 antigens on the cells are of the Ogawa type (with remainder consequently of the Inaba type). More preferably, 10-80% of the O1 antigens on the cells are of the Ogawa type, yet more preferably 10-50%, still more preferably 10-40% and most preferably 20-30%.

As shown in the Examples below, a suitable Hikojima phenotype as outlined above is obtainable by several distinct strategies utilizing recombinant DNA technology:

a) A mutant WbeT protein having low enzymatic activity may be expressed at high levels in a host having Inaba phenotype;
b) A WbeT protein having high enzymatic activity may be expressed at low levels in an Inaba host; or
c) The endogenous WbeT gene of an Ogawa host may be mutated e.g. by means of homologous recombination to render the resulting protein to have suitably reduced activity.
d) The endogenous WbeT gene of an Inaba host may be replaced or modified e.g. by means of homologous recombination to render the protein produced by the gene to have suitably increased activity.

The present invention discloses cells obtained by each of the above strategies, as well as DNA-constructs suitable for obtaining cells by each of the above strategies.

From the teachings herein it is apparent to the skilled person that achieving the desired level of WbeT expression by the strategies outlined above can be realized in many different ways. For instance, levels of expression of a WbeT transgene may be modulated by using an inducible promoter (such as cat, lac or tac) whereby the level of expression may be modulated during culture of the host cells by adjusting the level of the inducer that the host cells are exposed to.

Alternatively, several weak and strong constitutional promoters are also known and may be used in conjunction with a suitably modified WbeT protein. A weak promoter can be used to constitutionally induce a very low level of expression of a highly active (such as wild-type; SEQ ID NO: 6) WbeT protein. Conversely, a strong constitutional promoter can be used to induce a high level of expression of a WbeT protein having low activity (such as a mutated WbeT protein, preferably such as described below).

Both plasmids and chromosomally integrated wbeT transgenes may be used in the cells of the invention to achieve the desired phenotype.

Many different mutations of the WbeT-protein can potentially result in a suitably active protein, and such mutated variants can readily be obtained by the skilled person using methods well known in the arts by mere routine experimentation, on the basis of the teachings herein. Whether a cell of the desired phenotype is obtained by expressing the mutated WbeT protein or not can readily be analyzed by the skilled person e.g. using the methods disclosed in Example 5. The inventors have identified serine 158 in the WbeT protein (SEQ ID NO: 6) as a suitable residue to modulate activity. Thus, the mutations preferably comprise a substitution on serine 158, more preferably substitution of serine 158 to glycine, proline, valine, leucine, alanine, threonine, methionine, tryptophan, arginine or phenylalanine. Most preferably, the serine 158 is substituted by glycine, proline, threonine, phenylalanine or tryptophan.

ETEC Colonization Factor (CF) Protein(s)

As is evident from the above, the vaccine of the invention (or rather the cells on which the vaccine is based upon) may also comprise other enhanced features besides the combined expression of O1 antigens of both Inaba and Ogawa serotypes. In particular, the cells may express one or more ETEC colonization factor (CF) proteins, such as CFA/I, CS2 or CS5, wherein said CF protein(s) is/are expressed either as single, double, or hybrid fimbriae, as demonstrated in Example 7. Inclusion of such CF proteins in the cells of the vaccine is especially useful for inducing protective immunity against ETEC.

All references cited herein are hereby incorporated by reference in their entirety.

The expression "comprising" as used herein should be understood to include, but not be limited to, the stated items.

The invention is further illustrated by the following examples, which are to be seen as non-limiting.

Example 1

Preparation and Testing of a Vaccine Comprising *Vibrio cholerae* Cells Comprising O1 Antigens of Both Ogawa and Inaba Serotypes It was tested whether a vaccine comprising *V. cholerae* bacteria of strain JS1569 (Inaba) that had been genetically modified to express O1 antigens of both Ogawa and Inaba serotypes would give rise to an antibody response with a different proportion of antibodies reacting with Ogawa and Inaba LPS in ELISA as compared to the antibody response after immunization with the parent JS1569 Inaba strain.

The bacteria from example 2 (see below) were formalin-killed and used for immunization. Formalin-killing of bacteria and oral immunizations and assay methods were performed as previously described (Nygren E, Li B L, Holmgren J, Attridge S R. Infect Immun. 2009 August; 77(8):3475-84). Briefly, Balb/c mice were immunized in 3 rounds at 2-week intervals with two daily doses of 3×10⁸ formalin-killed cells (together with an adjuvant for the WbeT strain), and one week after the last immunization the mice were sacrificed and serum collected and tested for combined IgG/IgM antibody titers in ELISA plates coated with either Inaba or Ogawa LPS.

The results are presented in the table below and show that in contrast to the parent JS1569 Inaba strain which gave rise to an antibody response with a slightly higher anti-Inaba than anti-Ogawa titer, the JS1569/wild type Wbe S158S vaccine gave rise to an antibody response with a much higher anti-Ogawa than anti-Inaba titer, although it still gave rise also to modest formation of specific anti-Inaba antibodies:

| Immune serum | Inaba/Ogawa titers (Ratio) |
| --- | --- |
| To JS1569 | 10290/5060 (2:1) |
| Same absorbed with Ogawa | 2940/160 (18:1) |
| To JS1569/wild type Wbe S158S | 36000/365000 (1:10) |
| Same absorbed with Inaba | 1600/49000 (1:30) |
| Same absorbed with Ogawa | 1700/2500 (1:1.5) |

These findings were confirmed when immunizations were given subcutaneously without adjuvant. In marked difference to immunization with the parent JS1569 Inaba strain and more similar to immunization with the Ogawa A457 reference strain, immunization with J51569 WbeT gave rise to immune serum with a strong proportion of Ogawa specific antibodies, as shown in the table below.

| Immune serum | Inaba titer | Ogawa titer | Ratio Inaba/Ogawa |
| --- | --- | --- | --- |
| JS1569 Inaba | 480 | 260 | 1.8:1 |
| JS1569 abs with Ogawa A457 | 180 | 60 | 3:1 |
| JS1569 abs with 1569 WbeT | 240 | 60 | 4:1 |
| A457 Ogawa | 660 | 1940 | 1:1.9 |
| A457 abs with Inaba 1569 | 240 | 1020 | 1:4.3 |
| A457 abs with JS1569 WbeT | 180 | 40 | 1.8:1 |
| JS1569 WbeT | 420 | 1580 | 1:3.8 |
| WbeT abs with Ogawa A457 | 150 | 60 | 2.5:1 |
| WbeT abs with Inaba JS1569 | 180 | 920 | 1:5.1 |
| WbeT abs with JS1569 WbeT | 120 | 100 | 1.2:1 |

Example 2

Genetically Modified *Vibrio cholerae* Cells Expressing O1 Antigens of Both Ogawa and Inaba Serotypes by Expression of Mutated Wbet-Protein: Plasmid-Based Expression of Mutated Wbet-Protein In a single entry in GenBank of the wbeT gene from a Hikojima strain there is a mutation converting a serine to proline at position 158 of the protein (S158P) although the same mutation has been described in a strain identified as being of the Inaba serotype (GenBank accession numbers FJ619106 and DQ401028 respectively). Having amplified the wild-type wbeT gene from the O1 El Tor Ogawa strain VX44945 with primers wbeT1 EcoRI (SEQ ID NO: 15'-CCCGGTCTCGAATTC CTGCATCTGCAAGTTGAT-TCTGTATG-3') and wbeT2 HindIII (SEQ ID NO: 25'-CCCGGTCTCAAGCTTATAGTGAACTCTTCGGAAAT-GTCTG-3'), it was digested with Eco3I and cloned into an expression vector derived from pAF1 ( ) in which the cloned gene was placed under the control of the powerful synthetic tac promoter that had been digested with EcoRI and HindIII. The sequence of the gene was confirmed by DNA sequencing of the plasmid with primers wbe1 (SEQ ID NO: 35'-CTGCATCTGCAAGTTGATTCTGTATG-3') and wbe2 (SEQ ID NO: 45'-ATAGTGAACTCTTCGGAAAT-GTCTG-3').

The DNA sequence of the wild-type wbeT gene is shown in SEQ ID NO: 5 whereas the wild-type protein is shown in SEQ ID NO: 6.

The full sequence of the plasmid (pML-wbeTtac) expressing the wild-type wbeT is shown in SEQ ID NO: 7.

In order to construct the mutant library of wbeT carrying mutations at amino acid position 158 of the gene product, oligonucleotides wbeT m3 (SEQ ID NO: 85'-GCGCGCCA-GAACTTGGCTATTTTTAACC-3') and wbeT m1 (SEQ ID NO: 95'-GGGGGTTCGAAGTTTATGAGTTTGA-TAATAGGGTGNNBTCATTAT-ATTTTCAAAAAAATACA GACATAGCAGATAAGGT-TAAAAATAGCCAAGTTCTGGCGCGC-3') were synthesized. The two oligonucleotides were mixed in equimolar quantities and allowed to anneal at room temperature overnight. Full length double-stranded DNA was made by extension of the short wbeT m3 primer using T4 DNA polymerase in the presence of excess deoxyribonucleotide triphosphates. The resulting fragment was digested with Bsp119I and Van91I and ligated into pML-wbeTtac (SEQ ID NO: 7) digested with the same enzymes. The ligated DNA was used to transform commercially obtained electro-competent *E. coli* strain DH12S (Invitrogen). After incubation without antibiotic selection a small aliquot of the cells were spread onto a selective LB agar plate supplemented with ampicillin (100 μg/ml). The rest of the cells were diluted to 25 ml with fresh LB broth. Ampicillin was added to a final concentration of 100 μg/ml and the culture was grown overnight at 37° C. in order to obtain a clone library. Aliquots of the resulting culture were supplemented with glycerol to a final concentration of 17% and stored at −70° C. Other aliquots were used to prepare plasmid DNA.

The colonies obtained on the LB agar plate were picked onto a fresh plate and colonies were cultured to prepare plasmid DNA. The plasmids were sequenced in order to determine whether the wbeT genes carried mutations. Mutants of wbeT obtained from the library are the following: S158G, S158P, S158V, S158I, S158L, S158A, S158T, S158M, S158W, S158R, S158C and S158F. Additionally the wild-type gene and a gene with the stop signal TGA at position 158 were isolated.

The different plasmids were isolated and used to transform the O1 classical Inaba strain JS1569. This strain has a mutant wbeT gene with the glycine (GGA) at position 219 of the protein being changed to a stop codon (TGA) resulting in a truncated and inactive product (SEQ ID NO: 10 and SEQ ID NO: 11).

There are other polymorphisms that do not appear to have any significance.

The different strains generated by the introduction of the different recombinant plasmids expressed different levels of the Ogawa antigen when grown under inducing conditions (in the presence of 1 mM IPTG). The phenotype was assessed on the basis of agglutination assays and in some cases using inhibition ELISA (see Example 5 for description of materials and methods). The wild type gene gave rise to almost total serotype switching whereas others (such as S158P and S158G) gave slight but detectable agglutination with Ogawa-specific antiserum as well as agglutination with an Inaba-specific antiserum (and therefore conferred a Hikojima serotype). Some mutants had no detectable activity with Ogawa-specific antiserum (S158I and S158C) and yet others gave intermediate agglutination (S158T, S158F and S158W).

The results demonstrate unambiguously that mutations and specifically mutations at position 158 of the wbeT gene product result in proteins with altered enzyme activity. At present there is no reliable assay to directly quantitatively determine the levels of enzyme activity of these mutants compared to the wild-type, but the relevant end result can readily be evaluated as in Example 5. In summary, all except S158C and S158I were able to complement the Inaba phenotype of the host strain to some extent.

Example 3

Genetically Modified *Vibrio cholerae* Cells Expressing O1 Antigens of Both Ogawa and Inaba Serotypes by Expression of Mutated Wbet-Protein: Chromosomal Insertion of Mutant wbeT The truncated chromosomal wbeT gene in the strain JS1569 was substituted with the mutant genes generated in example 2. The relevant mutated genes were amplified with primers wbeT1 BlgII (SEQ ID NO: 1) and wbeT2 BglII (SEQ ID NO: 2). Amplified fragments were digested with BglII and ligated into the suicide vector pMT-SUICIDE (SEQ ID NO: 12) which had been digested with BamHI. This is a small R6K-based suicide vector constructed in this laboratory by M. Lebens which carries the chloramphenicol resistance gene and the origin of transfer (oriT) from the broad host-range plasmid RP4 that allows the plasmid to be conjugally transferred to *V. cholerae* strain with the aid of a helper plasmid (pNJ5000; Grinter N J, Gene. 1983 January-February; 21(1-2):133-43).

In the clones that were generated, the wbeT genes (S158G and the wild-type) were both inserted with the cloned genes in the opposite orientation to the cat gene. The sequence of such vector is exemplified by SEQ ID NO: 13 (carrying wild-type wbeT gene; the construct for S158G is identical save for the nucleotides coding for WbeT residue 158).

The resulting plasmids were mated into strain JS1569 and selected on the basis of chloramphenicol and rifampicin resistance. Since the plasmid has no counter-selection for loss of the plasmid, its insertion into the chromosome by homologous recombination results in tandem copies of the wbeT gene separated by the plasmid. Depending upon where the recombination occurred, the clones had different phenotypes (see Example 5).

The strain that had received the wild-type gene (1342) had a clear Hikojima phenotype. Inhibition ELISA showed that it expressed only 15% of the Ogawa LPS present on the surface of the strain that that received the S158G mutant. The latter strain (1356) was in effect an Ogawa strain that agglutinated strongly with Ogawa-specific antiserum, but not at all with the Inaba-specific antiserum.

The strains were however very stable; they retained their LPS serotypes and remained chloramphenicol resistant even in the absence of selection, indicating that the plasmid was not readily lost.

PCR and sequencing using the wbe1 and 2 primers (SEQ ID NO: 3 and 4, respectively) showed that there were two genes in the strains that varied at sites of variation between the gene present in the host and that which was introduced. Amplification and sequencing with primers wbeT for 87> (SEQ ID NO 14: 5'-CGGTGCAAACGTTG-GAACTTTCTG-3') and wbeT rev 51< (SEQ ID NO 15: 5'-GGAAAACAATGCCATCCAAATTCGC-3') that only allow amplification if there are tandem copies of the wbeT gene successfully amplified the 3' end of the proximal gene (from amino acid 87) and the 5' end of the distal gene up to amino acid 51 and the plasmid in between. Sequencing using the wbeT for 87> primer showed that in the strain 1342 the wbeT gene adjacent to the native promoter was the truncated host gene. The distal gene had the wild-type sequence but no promoter. This arrangement led to the Hikojima phenotype since the wild-type gene was being expressed at extremely low levels from a cryptic promoter.

In the Ogawa strain 1356 the arrangement was different. The recombination had resulted in the native wbeT gene being expressed from the native promoter and the mutant S158G gene being placed distally and therefore having no promoter recognizable at all. Both copies of the gene appear to have lost the stop codon at position 219, but this mutation had no apparent influence on the phenotype.

Example 4

Genetically Modified *Vibrio cholerae* Cells Expressing O1 Antigens of Both Ogawa and Inaba Serotypes by Expressing Low Levels of Native WbeT-Protein In conjunction with the experiments on mutant wbeT described in Example 2 it was noted that a control plasmid carrying the wild-type wbeT was able to partially complement the mutant gene in strain JS1569 even when it was not induced. This resulted in a Hikojima serotype even in the presence of the wild type gene demonstrating that the phenotype can also be achieved by limiting the levels of expression; in this case by keeping the tac promoter repressed and allowing only breakthrough expression that occurs in the absence of inducer.

In Example 3, the clone 1342 had a chromosomally integrated wild-type gene expressed from a cryptic promoter, which resulted in a Hikojima serotype. These results confirm that the expression of the wild-type gene at very low levels can result in the Hikojima serotype.

Example 5

Characterization of the Phenotype of Genetically Modified *Vibrio Cholerae* Cells

*V. cholerae* bacteria of strain JS1569 (Inaba) that had been modified to contain plasmids encoding for either the wild-type WbeT methylase protein (strain JS1569/S158S) or a mutated wbeT gene encoding for WbeT protein with a mutation in position 158 from S to G (JS1569/S158G) or from S to A (JS1569/S158A) were grown on LB agar plates, and single colonies were tested for agglutination by antibodies specific for Inaba and Ogawa O antigens, respectively.

These antibodies were obtained after first immunizing rabbits with purified Ogawa and Inaba LPS, respectively and then extensively absorbing the sera with formalin killed bacteria of the heterologous serotype in order to remove cross-reactive antibodies. After absorption, Ogawa-specific antiserum gave strong agglutination of reference *V. cholerae* cells of the Ogawa serotype but could not agglutinate Inaba cells and vice versa for the Inaba specific serum.

Agglutination tests were performed by standard method. Briefly, a single colony from a fresh plate of the tested strain was suspended in 50-100 μl physiological saline buffer, and 10 μl of the suspension was placed on a microscope slide. Then 10 μl of appropriately diluted specific antiserum was added and mixed with the cells by tilting the slide backwards and forwards for up to 5 minutes until agglutination was clearly visible. Each assay was compared with negative and positive controls consisting of cells from reference Inaba and Ogawa strains.

Additionally a control for spontaneous agglutination in which serum was replaced by buffer was performed for each strain tested. Results are shown in the table below and show that the JS1569/S158S strain containing plasmid encoding for wild-type WbeT protein had completely switched in serotype from Inaba to Ogawa, the JS1569/S158G strain with a WbeT 158S to G mutation expressed strong Ogawa but also detectable Inaba reactivity, and JS1569/S158A with a WbeT 158S to A mutation had only marginal Ogawa reactivity.

| Strain | WbeT encoding Plasmid | Agglutination with anti-Ogawa antibody | Agglutination with anti-Inaba antibody |
|---|---|---|---|
| JS1569 Inaba | None | − | +++ |
| Cairo 50 Ogawa | None | +++ | − |
| A457 Ogawa | None | +++ | − |
| JS1569/S158S | WbeT S158S wild-type | +++ | (+) |
| JS1569/S158G | WbeT S158G | ++ | ++ |
| JS1569/S158A | WbeT S158A | (+) | +++ |

These results were confirmed when formalin-killed bacteria of the same strains were tested for agglutination with the same sera. They were also confirmed and extended when the formalin-killed bacteria were tested for their quantitative expression of Inaba and Ogawa antigens on the bacterial surface using an ELISA-inhibition method. The method was performed as follows: High binding Greiner Bio-one plates were coated with Ogawa LPS by incubating overnight with 100 μl per well of a solution of 5 μg/ml purified Ogawa LPS in PBS. Starting with 200 microliter of $OD_{600}$ 1.00 formalin killed bacteria; seven serial five-fold dilutions were made (down to 1:15625) in PBS with an eighth blank tube containing no cells. 150 microliter of each dilution was mixed together with an equal amount of appropriately diluted anti-Ogawa serum in PBS, 0.2% BSA. The samples were incubated at room temperature for 1 hour without shaking. The coated plates were washed twice with PBS and blocked with 200 μl/well of PBS, 0.1% BSA for 30 minutes at 37° C. The cells were removed from the suspensions by centrifugation for 5 minutes at 20,000×g and 100 microliter of the supernatants were added to the blocked the plate(s). A blank containing PBS, 0.1% BSA with neither cells nor anti-Ogawa serum was included in all plates and all samples were run in duplicate. Plates were incubated for 1 hour at room temperature and then washed three times with PBS, 0.05% Tween 20. 100 microliter of appropriately diluted goat anti-rabbit IgG in PBS, 0.1% BSA, 0.05% Tween 20 was added to each well and incubated for 1 hour at room temperature. The plate was washed three times with PBS, 0.05% Tween 20 before adding the substrate solution of 0.1% ortpphenylenediamine (OPD) and 0.012% $H_2O_2$ in 0.1M citrate pH4.5. The absorbance was read at 490 nm after 10 min.

The bacterial dilution resulting in 50% inhibition was extrapolated and also the percentage inhibition of the absorbance at bacterial dilution of 1:25 with the results shown in the table below. The results show that the JS1569/S158S strain containing a wbeT gene encoding for wild-type WbeT could efficiently inhibit the specific anti-Ogawa serum, whereas the strains containing wbeT genes with single mutations could also inhibit the anti-Ogawa serum with intermediate activity (JS1569/S158G) or just detectably (JS1569/S158A):

| Strain | Dilution for 50% inhibition | % inhibition at dilution 1:25 |
|---|---|---|
| JS1569 Inaba | <<1:1 | 0 |
| A457 Ogawa | 1:60 | 65 |
| JS1569/S158G | 1:70 | 70 |
| JS1569/S158S | 1:1 | 20 |

Based on the plasmids encoding for WbeT and S158G, respectively, two recombinant derivative strains of JS1569, 1356 (wild-type WbeT) and 1342 (S158G WbeT), were obtained where the mutated wbeT gene had been stably inserted into the chromosome, giving unexpected but stable phenotypes. For an explanation and description of these strains see examples above. These strains and appropriate reference strains were subjected to colony blots for assaying Ogawa expression. Strains containing mutated wbeT genes were patched out on an LB agar plate together with Inaba and Ogawa control strains and grown overnight at 37° C. A nitrocellulose membrane moistened with PBS was applied on the plate with the grown out colonies and was left for 15 minutes at room temperature. The membrane was left to dry on a piece of paper for 5 minutes before it was blocked twice for 20 minutes in 10 ml of 1% Bovine serum albumin (BSA) in PBS at room temperature. The blocking liquid was discarded and replaced with an appropriate dilution of the anti-Ogawa serum in 10 ml in PBS containing 0.1% BSA and 0.05% Tween 20. The membrane was incubated at room temperature on a rocking table for 2 hours. The membrane was then washed three times with PBS containing 0.05% Tween20 before adding goat anti-rabbit IgG conjugated to horseradish peroxidase (Jackson Immunoresearch Laboratories Inc.) in 0.1% BSA in PBS with 0.05% Tween20 and incubating for 2 hours at room temperature with gentle agitation.

Following a further three washes in PSB, 0.05% Tween 20 and a single wash with PBS alone the membrane was developed for 15 minutes with 0.05% 4-chloro-1-naphtol and 0.015% $H_2O_2$ in 20 mM Tris-HCl pH 7.5 containing 500 mM NaCl and 16.7% methanol. It was then washed thoroughly with tap water and was left to dry on a piece of paper.

A digital photo was taken of the developed membrane and the staining density measured with a computer system.

Results in the table show that strain 1356 expressed almost as much Ogawa antigen as the Ogawa reference strain whereas strain 1342 expressed substantially lesser amounts of Ogawa antigen. These findings were further confirmed when formalin-killed preparations of the strains were tested for quantitative expression of Ogawa antigen by inhibition-ELISA done as described above as also shown in the table:

| Strain | Dot blot density units/mm$^2$ | Dilution for 50% inhibition |
|---|---|---|
| A 457 Ogawa | 12700 | 1:60 |
| JS1569 Inaba | 0 | <<1:1 |
| 1356 | 10000 | 1:80 |
| 1342 | 4500 | 1:7 |

Example 6

Genetic Modification of the Endogenous wbeT Gene to Obtain Hikojima Serotype

Although the strains presented in the above examples are stable and clearly have the desired phenotypes, an alternative manner of obtaining a Hikojima phenotype is to perform true gene substitutions in the endogenous gene. Suitable mutations (as disclosed above) at position 158 of the endogenous, active wbeT gene product also result in diminished activity and therefore a Hikojima serotype. This will result in a range of mutants with differing levels of Ogawa expression that can be tested for Hikojima expression as in Example 5 and in immunization experiments for the optimal immunogenic properties.

As mentioned, the pMT-SUICIDE vector lacks a suitable counter-selection gene and it has proved difficult isolate derivatives that have lost the plasmid and retain the desired gene and phenotype. For this reason a new suicide vector was constructed carrying the sacB gene from *Bacillus subtilis*, allowing strains that have lost the plasmid to be isolated by selection on plates containing sucrose since expression of the sacB gene product in gram-negative bacteria is lethal and only colonies derived from cells that have lost the plasmid due to homologous recombination between the two copies of the wbeT gene will survive. The plasmid, pMT Suicide/sacB (SEQ ID NO: 16) is much smaller than comparable plasmids with the same functions and is much easier to use.

The wild-type and a number of mutant wbeT genes have been cloned into the new vector and will be mated into the strain JS1569 as before, as well as to other strains such as a suitable Ogawa strain.

In order to optimize the chances of obtaining a correct clone the gene arrangement of the partial diploids that resulting from the transconjugation experiments will be analysed before a candidate strain is chosen for taking further for selection of strains that have recombined out the plasmid.

Example 7

Expression of hybrid CFA/I+CS2

It has recently been shown that *E. coli* TOP10 and *V. cholerae* JS1569 strains can express one of the major colonization factor of ETEC, i.e. CFA/I fimbriae, on their surface (Tobias J, Lebens M, Bolin I, Wiklund G, Svennerholm A M. Vaccine. 2008 Feb. 6; 26(6):743-52). Following electroporation of a CFA/1-containing expression vector into the above strains, the surface expression was detected by dot blot assay.

It has also recently been shown that *E. coli* TOP10 is capable of expressing a hybrid fimbriae containing the major subunits of both CFA/I and CS2—i.e. an additional major colonization factor of ETEC (Tobias J, Svennerholm A M, Holmgren J, Lebens M. Appl Microbiol Biotechnol. 2010 July; 87(4))

Therefore, we examined the feasibility of expression of the same hybrid fimbriae on *V. cholerae* JS1569. The strain was electroporated with the expression vector pJT-CFA/1-CotA as described (Tobias et al. 2008, supra; Tobias J, Holmgren J, Hellman M, Nygren E, Lebens M, Svennerholm A M. Vaccine. 2010 Aug. 20. [Epub ahead of print])

Fifty colonies (clones) were then streaked on two LB plates supplemented with chloramphenicol (12.5 μg/ml) and IPTG (1 mM), followed by over-night incubation at 37° C. Specific monoclonal antibodies (MAb) 1:6 against CFA/I and MAb 10:3 against CS2 were then applied in colony blot assay (Tobias et al, 2010, supra) to examine the surface expression of the hybrid CFA/1-CotA fimbrie on *V. cholerae* JS1569. The blots were then developed and showed positive signal of surface expression of the hybrid CFA/1-M fimbriae on all tested fifty clones of *V. cholerae* JS1569.

Thus it is possible to combine the expression of antigenic hybrid fimbriae in the same cells that have been engineered to express O1 antigens of both Ogawa and Inaba serotypes.

We claim:

1. A vaccine comprising multiple *Vibrio cholerae* O1 cells, wherein the cells simultaneously express O1 antigens of both Ogawa and Inaba serotypes, wherein between 10-90% of the O1 antigens expressed by the cells are of the Ogawa-serotype, and wherein the cells are formalin inactivated.

2. A vaccine according to claim 1, wherein the cells further comprise one or more enterotoxigenic *E. coli* (ETEC) colonization factor (CF) protein(s).

3. A vaccine according to claim 1, wherein said vaccine does not contain any further immunogically active whole cells in addition to *Vibrio cholerae* O1 cells that comprise O1 antigens of both Ogawa and Inaba serotypes.

4. A vaccine according to claim 1, wherein the vaccine is formulated for oral administration.

5. A vaccine according to claim 1, wherein the cell is a cell in which:
   a. the endogenous wbeT-gene of the cell or the protein coded thereof is inactive;
   b. the cell comprises a recombinant DNA-construct expressing a WbeT enzyme having WbeT enzyme activity; and wherein
   c. the level of the WbeT enzyme activity of the WbeT enzyme expressed in step b) is such that the cell simultaneously expresses Inaba and Ogawa antigens;
   wherein the cells comprise a recombinant Wbe T-protein having at least 99% sequence identity to SEQ ID NO: 6 and comprising a substitution of the serine residue in position 158 of SEQ ID No: 6.

6. A *Vibrio cholerae* O1 cell simultaneously expressing both Inaba and Ogawa antigens, characterized in that a) the endogenous wbeT-gene of the cell or the protein coded thereof is inactive;
b) the cell comprises a recombinant DNA-construct expressing a WbeT enzyme having WbeT enzyme activity; and wherein
c) the level of the WbeT enzyme activity of the WbeT enzyme expressed in step b) is such that the cell simultaneously expresses Inaba and Ogawa antigens; wherein the cell comprises a recombinant Wbe T-protein having at least 99% sequence identity to SEQ ID NO: 6 and comprising a substitution of the serine residue in position 158 of SEQ ID No: 6.

7. A *Vibrio cholerae* O1 cell according to claim 6 wherein the recombinant DNA-construct is a DNA-construct comprising DNA coding for a WbeT-protein having at least 99% sequence identity to SEQ ID NO: 6 operatively coupled to a promoter suitable for inducing protein expression in a *Vibrio cholerae* O1 host cell, wherein the coded WbeT-protein comprises a sequence modification in relation to SEQ ID NO: 6 that reduces the enzymatic activity of the coded protein relative to the enzymatic activity of a protein with a sequence identical to SEQ ID NO: 6, wherein said sequence modification in relation to SEQ ID NO:6 comprises a substitution at serine 158.

8. A *Vibrio cholerae* O1 cell according to claim 6, wherein 10-90% of the O1 antigen expressed by the cell is of the Ogawa-serotype.

9. A *Vibrio cholerae* O1 cell according to claim 6, wherein the cell further express one or more enterotoxigenic coil (ETEC) colonization factor protein(s).

10. A *Vibrio cholerae* O1 cell according to claim 6 wherein the recombinant DNA-construct comprises DNA coding for a WbeT-protein having at least 99% sequence identity to SEQ ID NO: 6 operatively coupled to a promoter suitable for inducing protein expression in a *Vibrio cholerae* O1 host cell, wherein the promoter is suitable for inducing the expression of the coded WbeT-protein in a *Vibrio cholerae* O1 host cell initially of Inaba phenotype to such level of transgenic WbeT protein expression as to allow simultaneous expression of both Inaba and Ogawa antigens by the host cell, wherein said sequence modification in relation to SEQ ID NO:6 comprises a substitution at serine 158.

* * * * *

SEQUENCE LISTING

```
<160> NUMBER OF SEQ ID NOS: 16

<210> SEQ ID NO 1
<211> LENGTH: 41
<212> TYPE: DNA
<213> ORGANISM: Vibrio cholerae

<400> SEQUENCE: 1
cccggtctcg aattcctgca tctgcaagtt gattctgtat g                      41

<210> SEQ ID NO 2
<211> LENGTH: 40
<212> TYPE: DNA
<213> ORGANISM: Vibrio cholerae
```

-continued

<400> SEQUENCE: 2
cccggtctca agcttatagt gaactcttcg gaaatgtctg     40

<210> SEQ ID NO 3
<211> LENGTH: 26
<212> TYPE: DNA
<213> ORGANISM: Vibrio cholerae

<400> SEQUENCE: 3
ctgcatctgc aagttgattc tgtatg     26

<210> SEQ ID NO 4
<211> LENGTH: 25
<212> TYPE: DNA
<213> ORGANISM: Vibrio cholerae

<400> SEQUENCE: 4
atagtgaact cttcggaaat gtctg     25

<210> SEQ ID NO 5
<211> LENGTH: 953
<212> TYPE: DNA
<213> ORGANISM: Vibrio cholerae
<220> FEATURE:
<221> NAME/KEY: CDS
<222> LOCATION: (67)..(927)

<400> SEQUENCE: 5

```
cctgcatctg caagttgatt ctgtatgtta tttttacgc taatattatt taaaattgag       60 gtagta atg aaa cat cta ata aaa aac tat gta caa aaa tta att aaa       108
       Met Lys His Leu Ile Lys Asn Tyr Val Gln Lys Leu Ile Lys
       1               5                   10 aca gag ctt gat gct att cag tca aag tct gtt cat gat aat cga aac       156
Thr Glu Leu Asp Ala Ile Gln Ser Lys Ser Val His Asp Asn Arg Asn
15                  20                  25                  30 ttc att tac aat gga gag ttt tta att ctt gaa agc gaa ttt gga tgg       204
Phe Ile Tyr Asn Gly Glu Phe Leu Ile Leu Glu Ser Glu Phe Gly Trp
                35                  40                  45 cat tgt ttt ccc aga gtg cag ttg aac cat gct tta agc tac aaa aac       252
His Cys Phe Pro Arg Val Gln Leu Asn His Ala Leu Ser Tyr Lys Asn
            50                  55                  60 cca aac ttt gat tta ggt atg cgt cac tgg att gtt aat cat tgt aag       300
Pro Asn Phe Asp Leu Gly Met Arg His Trp Ile Val Asn His Cys Lys
        65                  70                  75 cat gac acc act tat att gat atc ggt gca aac gtt gga act ttc tgt       348
His Asp Thr Thr Tyr Ile Asp Ile Gly Ala Asn Val Gly Thr Phe Cys
    80                  85                  90 gga atc gct gct cgt cat att aca caa gga aaa att ata gcg ata gaa       396
Gly Ile Ala Ala Arg His Ile Thr Gln Gly Lys Ile Ile Ala Ile Glu
95                  100                 105                 110 cca ctc aca gaa atg gaa aat agt att agg atg aat gtt caa tta aat       444
Pro Leu Thr Glu Met Glu Asn Ser Ile Arg Met Asn Val Gln Leu Asn
                115                 120                 125 aat cca ctg gtt gag ttt cat cat ttt ggc tgt gca ata ggt gag aat       492
Asn Pro Leu Val Glu Phe His His Phe Gly Cys Ala Ile Gly Glu Asn
            130                 135                 140 gaa ggg gaa aat att ttc gaa gtt tat gag ttt gat aat agg gtg tca       540
Glu Gly Glu Asn Ile Phe Glu Val Tyr Glu Phe Asp Asn Arg Val Ser
        145                 150                 155 tca tta tat ttt caa aaa aat aca gac ata gca gat aag gtt aaa aat       588
Ser Leu Tyr Phe Gln Lys Asn Thr Asp Ile Ala Asp Lys Val Lys Asn
```

```
          160                 165                 170
agc caa gtt ctg gtt aga aag tta agt agt tta gat ata tcg cct act    636
Ser Gln Val Leu Val Arg Lys Leu Ser Ser Leu Asp Ile Ser Pro Thr
175                 180                 185                 190 aac tct gta gtt ata aaa att gat gct gaa ggc gca gaa ata gag ata    684
Asn Ser Val Val Ile Lys Ile Asp Ala Glu Gly Ala Glu Ile Glu Ile
                195                 200                 205 tta aac cag att tac gaa ttc aca gaa aag cat aat gga att gaa tat    732
Leu Asn Gln Ile Tyr Glu Phe Thr Glu Lys His Asn Gly Ile Glu Tyr
            210                 215                 220 tat att tgc ttt gaa ttt gca atg ggt cat ata cag agg tct aat aga    780
Tyr Ile Cys Phe Glu Phe Ala Met Gly His Ile Gln Arg Ser Asn Arg
        225                 230                 235 act ttt gat gag att ttt aac ata ata aac tca aaa ttc gga agt aag    828
Thr Phe Asp Glu Ile Phe Asn Ile Ile Asn Ser Lys Phe Gly Ser Lys
240                 245                 250 gca tat ttt att cat cca tta tca tcc gct gaa cat cct gag ttt aat    876
Ala Tyr Phe Ile His Pro Leu Ser Ser Ala Glu His Pro Glu Phe Asn
255                 260                 265                 270 aaa gca acg cag gat att aat ggg aat atc tgt ttt aaa tat gta tca    924
Lys Ala Thr Gln Asp Ile Asn Gly Asn Ile Cys Phe Lys Tyr Val Ser
                275                 280                 285 taa aataattttaa tatattccgt atgtca                                  953
```

<210> SEQ ID NO 6
<211> LENGTH: 286
<212> TYPE: PRT
<213> ORGANISM: Vibrio cholerae

<400> SEQUENCE: 6

```
Met Lys His Leu Ile Lys Asn Tyr Val Gln Lys Leu Ile Lys Thr Glu
1               5                   10                  15

Leu Asp Ala Ile Gln Ser Lys Ser Val His Asp Asn Arg Asn Phe Ile
            20                  25                  30

Tyr Asn Gly Glu Phe Leu Ile Leu Glu Ser Glu Phe Gly Trp His Cys
        35                  40                  45

Phe Pro Arg Val Gln Leu Asn His Ala Leu Ser Tyr Lys Asn Pro Asn
    50                  55                  60

Phe Asp Leu Gly Met Arg His Trp Ile Val Asn His Cys Lys His Asp
65                  70                  75                  80

Thr Thr Tyr Ile Asp Ile Gly Ala Asn Val Gly Thr Phe Cys Gly Ile
                85                  90                  95

Ala Ala Arg His Ile Thr Gln Gly Lys Ile Ile Ala Ile Glu Pro Leu
            100                 105                 110

Thr Glu Met Glu Asn Ser Ile Arg Met Asn Val Gln Leu Asn Asn Pro
        115                 120                 125

Leu Val Glu Phe His His Phe Gly Cys Ala Ile Gly Glu Asn Glu Gly
    130                 135                 140

Glu Asn Ile Phe Glu Val Tyr Glu Phe Asp Asn Arg Val Ser Ser Leu
145                 150                 155                 160

Tyr Phe Gln Lys Asn Thr Asp Ile Ala Asp Lys Val Lys Asn Ser Gln
                165                 170                 175

Val Leu Val Arg Lys Leu Ser Ser Leu Asp Ile Ser Pro Thr Asn Ser
            180                 185                 190

Val Val Ile Lys Ile Asp Ala Glu Gly Ala Glu Ile Glu Ile Leu Asn
        195                 200                 205
```

```
Gln Ile Tyr Glu Phe Thr Glu Lys His Asn Gly Ile Glu Tyr Tyr Ile
        210                 215                 220

Cys Phe Glu Phe Ala Met Gly His Ile Gln Arg Ser Asn Arg Thr Phe
225                 230                 235                 240

Asp Glu Ile Phe Asn Ile Ile Asn Ser Lys Phe Gly Ser Lys Ala Tyr
                245                 250                 255

Phe Ile His Pro Leu Ser Ser Ala Glu His Pro Glu Phe Asn Lys Ala
                260                 265                 270

Thr Gln Asp Ile Asn Gly Asn Ile Cys Phe Lys Tyr Val Ser
                275                 280                 285

<210> SEQ ID NO 7
<211> LENGTH: 4858
<212> TYPE: DNA
<213> ORGANISM: Artificial Sequence
<220> FEATURE:
<223> OTHER INFORMATION: Synthetic plasmid

<400> SEQUENCE: 7
```

| | | | | | |
|---|---|---|---|---|---|
| aggtggcact | tttcggggaa | atgtgcgcgg | aaccccctatt | tgtttatttt | tctaaataca | 60 |
| ttcaaatatg | tatccgctca | tgagacaata | accctgataa | atgcttcaat | aatccggatt | 120 |
| gaaaaaggaa | gagtatgagt | attcaacatt | tccgtgtcgc | ccttattccc | ttttttgcgg | 180 |
| cattttgcct | tcctgttttt | gctcacccag | aaacgctggt | gaaagtaaaa | gatgctgaag | 240 |
| atcagttggg | tgcacgagtg | ggttacatcg | aactggatct | caacagcggt | aagatccttg | 300 |
| agagttttcg | ccccgaagaa | cgttttccaa | tgatgagcac | ttttaaagtt | ctgctatgtg | 360 |
| gcgcggtatt | atcccgtgtt | gacgccgggc | aagagcaact | cggtcgccgc | atacactatt | 420 |
| ctcagaatga | cttggttgag | tactcaccag | tctcagaaaa | gcatcttacg | gatggcatga | 480 |
| cagtaagaga | attatgcagt | gctgccataa | ccatgagtga | taacactgcg | gccaacttac | 540 |
| ttctgacaac | gatcggagga | ccgaaggagc | taaccgcttt | tttgcacaac | atgggggatc | 600 |
| atgtaactcg | ccttgatcgt | tgggaaccgg | agctgaatga | agccatacca | aacgacgagc | 660 |
| gtgacaccac | gatgcctgta | gcaatggcaa | caacgttgcg | caaactatta | actggcgaac | 720 |
| tacttactct | agcttcccgg | caacaattaa | tagactggat | ggaggcggat | aaagttgcag | 780 |
| gaccacttct | gcgctcggcc | cttccggctg | gctggtttat | tgctgataaa | tctggagccg | 840 |
| gtgagcgtgg | gtctcgcggt | atcattgcag | cactggggcc | agatggtaag | ccctcccgta | 900 |
| tcgtagttat | ctacacgacg | gggagtcagg | caactatgga | tgaacgaaat | agacagatcg | 960 |
| ctgagatagg | tgcctcactg | attaagcatt | ggtaactgtc | agaccaagtt | tactcatata | 1020 |
| tactttagat | tgatttaaaa | cttcatttt | aatttaaaag | gatctaggtg | aagatccttt | 1080 |
| ttgataatct | catgaccaaa | atcccttaac | gtgagttttc | gttccactga | gcgtcagacc | 1140 |
| ccgtagaaaa | gatcaaagga | tcttcttgag | atcctttttt | tctgcgcgta | atctgctgct | 1200 |
| tgcaaacaaa | aaaaccaccg | ctaccagcgg | tggtttgttt | gccggatcaa | gagctaccaa | 1260 |
| ctctttttcc | gaaggtaact | ggcttcagca | gagcgcagat | accaaatact | gtccttctag | 1320 |
| tgtagccgta | gttaggccac | cacttcaaga | actctgtagc | accgcctaca | tacctcgctc | 1380 |
| tgctaatcct | gttaccagtg | gctgctgcca | gtggcgataa | gtcgtgtctt | accgggttgg | 1440 |
| actcaagacg | atagttaccg | gataaggcgc | agcggtcggg | ctgaacgggg | ggttcgtgca | 1500 |
| cacagcccag | cttggagcga | acgacctaca | ccgaactgag | atacctacag | cgtgagcatt | 1560 |
| gagaaagcgc | cacgcttccc | gaagggagaa | aggcggacag | gtatccggta | agcggcaggg | 1620 |

```
tcggaacagg acagcgcacg agggagcttc caggggggaaa cgcctggtat ctttatagtc    1680
ctgtcgggtt tcgccacctc tgacttgagc gtcgattttt gtgatgctcg tcagggggc     1740 ggagcctatg gaaaatcttt cctgcgttat ccctgattc tgtggataac cgtattaccg     1800
cctttgagtg agctgacgcc agcaacgcgg cctttttacg gttcctggcc ttttgctggc    1860
cttttgctca catgttcttt cctgcgttat ccctgattc tgtggataac cgtattaccg     1920
cctttgagtg agctgatacc gctcgccgca gccgaacgac cgagcgcagc gagtcagtga    1980
gcgaggaagc ggaagagcgc ctgatgcggt attttctcct tacgcatctg tgcggtattt    2040
cacaccgcat atggtgcact ctcagtacaa tctgctctga tgccgcatag ttaagccagt    2100
atacactccg ctatcgctac gtgactgggt catggctgcg ccccgacacc cgccaacacc    2160
cgctgacgcg ccctgacggg cttgtctgct cccggcatcc gcttacagac aagctgtgac    2220
cgtctccggg agctgcatgt gtcagaggtt ttcaccgtca tcaccgaaac gcgcgaggca    2280
ggatcccgaa cgccagcaag acgtagccca gcgcgtcggc cagcttgcaa ttcgcgctaa    2340
ctcacattaa ttgcgttgcg ctcactgccc gctttccagt cgggaaacct gtcgtgccag    2400
ctgcattaat gaatcggcca acgcgcgggg agaggcggtt tgcgtattgg gcgccagggt    2460 ggttttctt ttcaccagtg agacgggcaa cagctgattg cccttcaccg cctggccctg     2520
agagagttgc agcaagcggt ccacgctggt ttgccccagc aggcgaaaat cctgtttgat    2580
ggtggttaac ggcgggatat aacatgagct gtcttcggta tcgtcgtatc ccactaccga    2640
gatatccgca ccaacgcgca gcccggactc ggtaatggcg cgcattgcgc ccagcgccat    2700
ctgatcgttg gcaaccagca tcgcagtggg aacgatgccc tcattcagca tttgcatggt    2760
ttgttgaaaa ccggacatgg cactccagtc gccttcccgt tccgctatcg gctgaatttg    2820
attgcgagtg agatatttat gccagccagc cagacgcaga cgcgccgaga cagaacttaa    2880
tgggcccgct aacagcgcga tttgctggtg acccaatgcg accagatgct ccacgcccag    2940
tcgcgtaccc tcttcatggg agaaaataat actgttgatg ggtgtctggt cagagacatc    3000
aagaaataac gccggaacat tagtgcaggc agcttccaca gcaatggcat cctggtcatc    3060
cagcggatag ttaatgatca gcccactgac gcgttgcgcg agaagattgt gcaccgccgc    3120
tttacaggct tcgacgccgc ttcgttctac catcgacacc accacgctgg cacccagttg    3180
atcggcgcga gatttaatcg ccgcgacaat ttgcgacggc gcgtgcaggg ccagactgga    3240
ggtggcaacg ccaatcagca acgactgttt gcccgccagt tgttgtgcca cgcggttggg    3300
aatgtaattc agctccgcca tcgccgcttc acttttttcc cgcgttttcg cagaaacgtg    3360
gctggcctgg ttcaccacgc gggaaacggt ctgataagag acaccggcat actctgcgac    3420
atcgtataac gttactggtt tcacattcac caccctgaat tgactctctt ccgggcgcta    3480
tcatgccata ccgcgaaagg ttttgcacca ttcgatggtg tcaacgtaaa tgccgcttcg    3540
ccttcgcgcg cgaattgcaa gctgatccgg gcttatcgac tgcacggtgc accaatgctt    3600
ctggcgtcag gcagccatcg gaagctgtgg tatggctgtg caggtcgtaa atcactgcat    3660
aattcgtgtc gctcaaggcg cactcccgtt ctggataatg ttttttgcgc cgacatcata    3720
acggttctgg cagatctgaa atgagctgtt gacaattaat catcggctcg tataatgtgt    3780
ggaattgtga gcggataaca atttcacaca ggaaacagaa ttcctgcatc tgcaagttga    3840
ttctgtatgt tatttttac gctaatatta tttaaaattg aggtagtatg aaacatctaa     3900
taaaaaacta tgtacaaaaa ttaattaaaa cagagcttga tgctattcag tcaaagtctg    3960
ttcatgataa tcgaaacttc atttacaatg gagagttttt aattcttgaa agcgaatttg    4020
```

-continued

```
gatggcattg ttttcccaga gtgcagttga accatgcttt aagctacaaa aacccaaact    4080
ttgatttagg tatgcgtcac tggattgtta atcattgtaa gcatgacacc acttatattg    4140
atatcggtgc aaacgttgga actttctgtg gaatcgctgc tcgtcatatt acacaaggaa    4200
aaattatagc gatagaacca ctcacagaaa tggaaaatag tattaggatg aatgttcaat    4260
taaataatcc actagttgag tttcatcatt ttggctgtgc aataggtgag aatgaagggg    4320
aaaatatttt cgaagtttat gagtttgata atagggtgtc atcattatat ttcaaaaaaa    4380
atacagacat agcagataag gttaaaaata gccaagttct ggttagaaag ttaagtagtt    4440
tagatatatc gcctactaac tctgtagtta taaaaattga tgctgaaggc gcagaaatag    4500
agatattaaa ccagatttac gaattcacag aaaagcataa tggaattgaa tattatattt    4560
gctttgaatt tgcaatgggt catatacaga ggtctaatag aactttcgat gagattttta    4620
acataataaa ctcaaaattc ggaagtaagg catatttat  tcatccatta tcatccgctg    4680
aacatcctga gttaataaaa gcaacgcagg atattaatgg gaatatctgt tttaaatatg    4740
tatcataaaa taatttaata tattctcgta tgtcattgca agttcaacag acatttccga    4800
agagttcact ataagcttag cccgcctaat gagcgggctt tttttctcg aggacgtc      4858
```

<210> SEQ ID NO 8
<211> LENGTH: 28
<212> TYPE: DNA
<213> ORGANISM: Vibrio cholerae

<400> SEQUENCE: 8

```
gcgcgccaga acttggctat ttttaacc                                        28
```

<210> SEQ ID NO 9
<211> LENGTH: 104
<212> TYPE: DNA
<213> ORGANISM: Vibrio cholerae
<220> FEATURE:
<221> NAME/KEY: misc_feature
<222> LOCATION: (36)..(37)
<223> OTHER INFORMATION: n denotes a, t, c or g
<220> FEATURE:
<221> NAME/KEY: misc_feature
<222> LOCATION: (38)..(38)
<223> OTHER INFORMATION: b denotes c or g or t

<400> SEQUENCE: 9

```
gggggttcga agtttatgag tttgataata gggtgnnbtc attatatttt caaaaaaata    60
cagacatagc agataaggtt aaaaatagcc aagttctggc gcgc                     104
```

<210> SEQ ID NO 10
<211> LENGTH: 934
<212> TYPE: DNA
<213> ORGANISM: Vibrio cholerae
<220> FEATURE:
<221> NAME/KEY: CDS
<222> LOCATION: (22)..(678)

<400> SEQUENCE: 10

```
attatttaaa ttgaggtagt a atg aaa cat cta ata aaa aac tat gta caa       51
                       Met Lys His Leu Ile Lys Asn Tyr Val Gln
                        1               5                  10 aaa tta att aaa aca gag ctt gat gct att cag tca aag tct gtt cat      99
Lys Leu Ile Lys Thr Glu Leu Asp Ala Ile Gln Ser Lys Ser Val His
         15                  20                  25 gat aat cga aac ttc att tac aat gga gag ttt tta att ctt gaa agc     147
```

```
                            Asp Asn Arg Asn Phe Ile Tyr Asn Gly Glu Phe Leu Ile Leu Glu Ser
                                            30                  35                  40 gaa ttt gga ttg cat tgt ttt ccc aga gtg cag ttg aac cat gct tta         195
Glu Phe Gly Leu His Cys Phe Pro Arg Val Gln Leu Asn His Ala Leu
            45                  50                  55 agc tac aaa aac cca aac ttt gat tta ggt atg cgt cac tgg att gtt         243
Ser Tyr Lys Asn Pro Asn Phe Asp Leu Gly Met Arg His Trp Ile Val
    60                  65                  70 aat cat tgt aag cat gac acc act tat att gat atc ggt gca aac gtt         291
Asn His Cys Lys His Asp Thr Thr Tyr Ile Asp Ile Gly Ala Asn Val
75                  80                  85                  90 gga act ttc tgt gga atc gct gct cgt cat ata cac caa gga aaa att         339
Gly Thr Phe Cys Gly Ile Ala Ala Arg His Ile His Gln Gly Lys Ile
                95                  100                 105 ata gcg ata gaa cca ctc aca gaa atg gaa aat agt att agg atg aat         387
Ile Ala Ile Glu Pro Leu Thr Glu Met Glu Asn Ser Ile Arg Met Asn
        110                 115                 120 gtt caa tta aat aat cca cta gtt gag ttt cat cat ttt ggc tgt gca         435
Val Gln Leu Asn Asn Pro Leu Val Glu Phe His His Phe Gly Cys Ala
    125                 130                 135 ata ggt gag aat gaa ggg gaa aat att ttc gaa gtt tat gag ttt gat         483
Ile Gly Glu Asn Glu Gly Glu Asn Ile Phe Glu Val Tyr Glu Phe Asp
140                 145                 150 aat agg gtg tca tca tta tat ttt aaa aaa aat aca gac ata gca gat         531
Asn Arg Val Ser Ser Leu Tyr Phe Lys Lys Asn Thr Asp Ile Ala Asp
155                 160                 165                 170 aag gtt aaa aat agc caa gtt ctg gtt aga aag tta agt agt tta gat         579
Lys Val Lys Asn Ser Gln Val Leu Val Arg Lys Leu Ser Ser Leu Asp
                175                 180                 185 ata tcg cct act aac tct gta gtt ata aaa att gat gct gaa ggc gca         627
Ile Ser Pro Thr Asn Ser Val Val Ile Lys Ile Asp Ala Glu Gly Ala
        190                 195                 200 gaa ata gag ata tta aac cag att tac gaa ttc aca gaa aag cat aat         675
Glu Ile Glu Ile Leu Asn Gln Ile Tyr Glu Phe Thr Glu Lys His Asn
    205                 210                 215 tga attgaatatt atatttgctt tgaatttgca atgggtcata tacagaggtc              728
taatagaact tttgatgaga ttttttaacat aataaactca aaattcggaa gtaaggcata     788
ttttattcat ccattatcat ccgctgaaca tcctgagttt aataaagcaa cgcaggatat      848
taatgggaat atctgtttta aatatgtatc ataaaataat ttaatatatt ccgtatgtca      908
ttgcaagttc aacagacatt tcgaga                                            934

<210> SEQ ID NO 11
<211> LENGTH: 218
<212> TYPE: PRT
<213> ORGANISM: Vibrio cholerae

<400> SEQUENCE: 11

Met Lys His Leu Ile Lys Asn Tyr Val Gln Lys Leu Ile Lys Thr Glu
1               5                   10                  15

Leu Asp Ala Ile Gln Ser Lys Ser Val His Asp Asn Arg Asn Phe Ile
            20                  25                  30

Tyr Asn Gly Glu Phe Leu Ile Leu Glu Ser Glu Phe Gly Leu His Cys
        35                  40                  45

Phe Pro Arg Val Gln Leu Asn His Ala Leu Ser Tyr Lys Asn Pro Asn
    50                  55                  60

Phe Asp Leu Gly Met Arg His Trp Ile Val Asn His Cys Lys His Asp
65                  70                  75                  80
```

Thr Thr Tyr Ile Asp Ile Gly Ala Asn Val Gly Thr Phe Cys Gly Ile
            85                  90                  95

Ala Ala Arg His Ile His Gln Gly Lys Ile Ile Ala Ile Glu Pro Leu
            100                 105                 110

Thr Glu Met Glu Asn Ser Ile Arg Met Asn Val Gln Leu Asn Asn Pro
            115                 120                 125

Leu Val Glu Phe His His Phe Gly Cys Ala Ile Gly Glu Asn Glu Gly
        130                 135                 140

Glu Asn Ile Phe Glu Val Tyr Glu Phe Asp Asn Arg Val Ser Ser Leu
145                 150                 155                 160

Tyr Phe Lys Lys Asn Thr Asp Ile Ala Asp Lys Val Lys Asn Ser Gln
            165                 170                 175

Val Leu Val Arg Lys Leu Ser Ser Leu Asp Ile Ser Pro Thr Asn Ser
            180                 185                 190

Val Val Ile Lys Ile Asp Ala Glu Gly Ala Glu Ile Glu Ile Leu Asn
            195                 200                 205

Gln Ile Tyr Glu Phe Thr Glu Lys His Asn
    210                 215

<210> SEQ ID NO 12
<211> LENGTH: 1954
<212> TYPE: DNA
<213> ORGANISM: Artificial
<220> FEATURE:
<223> OTHER INFORMATION: Synthetic plasmid

<400> SEQUENCE: 12
agtaatacga ctcactagtg ggcagatctt cgaatgcatc gcgcgcaccg tacgtctcga      60
ggaattcctg caggatatct ggatccacga agcttcccat ggtgacgtca ccggttctag     120
atacctaggt gagctctggt accctctagt caaggcctgt cagccgttaa gtgttcctgt     180
gtcactgaaa attgctttga gaggctctaa gggcttctca gtgcgttaca tccctggctt     240
gttgtccaca accgttaaac cttaaaagct ttaaaagcct tatatattct ttttttttctt    300 ataaaactta aaaccttaga ggctatttaa gttgctgatt tatattaatt ttattgttca     360
aacatgagag cttagtacgt gaaacatgag agcttagtac gttagccatg agagcttagt     420
acgttagcca tgagggttta gttcgttaaa catgagagct tagtacgtta acatgagag      480 cttagtacgt gaaacatgag agcttagtac gtactatcaa caggttgaac tgctgatctt     540
cagatctccg cttgccctca tctgttacgc cggcggtagc cggccagcct cgcagagcag     600
gattcccgtt gagcaccgcc aggtgcgaat aagggacagt gaagaaggaa caccgctcg     660 cgggtgggcc tacttcacct atcctgcccg gctgacgccg ttggatacac caaggaaagt     720
ctacacgaac cctttggcaa atcctgtatat tcgtgcgaa aaaggatgga tataccgaaa     780
aaatcgctat aatgaccccg aagcagggtt atgcagcgga aaagcgctgc ttccctgctg     840
ttttgtggaa tatctaccga ctggaaacag gcaaatgcag gaaattactg aactgagggg     900
acaggcgaga gatctggcct aggccgaccg aataaatacc tgtgacggaa gatcacttcg     960
cagaataaat aaatcctggt gtccctgttg ataccgggaa gccctgggcc aacttttggc    1020
gaaaatgaga cgttgatcgg cacgtaagag gttccaactt tcaccataat gaaataagat    1080
cactaccggg cgtattttttt gagttgtcga gattttcagg agctaaggaa gctaaaatgg    1140
agaaaaaaat cactggatat accaccgttg atatatccca atggcatcgt aaagaacatt    1200
ttgaggcatt tcagtcagtt gctcaatgta cctataacca gaccgttcag ctggatatta    1260

```
cggcctttt  aaagaccgta  aagaaaaata  agcacaagtt  ttatccggcc  tttattcaca    1320
ttcttgcccg  cctgatgaat  gctcatccgg  aattacgtat  ggcaatgaaa  gacggtgagc    1380
tggtgatatg  ggatagtgtt  cacccttgtt  acaccgtttt  ccatgagcaa  actgaaacgt    1440
tttcatcgct  ctggagtgaa  taccacgacg  atttccggca  gtttctacac  atatattcgc    1500
aagatgtggc  gtgttacggt  gaaaacctgg  cctatttccc  taaagggttt  attgagaata    1560 tgttttcgt  ctcagccaat  ccctgggtga  gtttcaccag  ttttgattta  aacgtggcca    1620
atatggacaa  cttcttcgcc  cccgttttca  ccatgggcaa  atattatacg  caaggcgaca    1680
aggtgctgat  gccgctggcg  attcaggttc  atcatgccgt  ttgtgatggc  ttccatgtcg    1740
gcagaatgct  taatgaatta  caacagtact  gcgatgagtg  gcagggcggg  gcgtaatttt    1800
tttaaggcag  ttattggtgc  ccataaacgc  ctggttgcta  cgcctgaata  agtgataata    1860
agcggatgaa  tggcagaaat  tcgaaagcaa  attcgacccg  gtcgtcggtt  cagggcaggg    1920
tcgttaaata  gccgcttatg  tctattgctg  gttt                                 1954

<210> SEQ ID NO 13
<211> LENGTH: 2948
<212> TYPE: DNA
<213> ORGANISM: Artificial
<220> FEATURE:
<223> OTHER INFORMATION: Synthetic vector construct with wild-type wbeT
      insert
<220> FEATURE:
<221> NAME/KEY: misc_feature
<222> LOCATION: (151)..(1011)
<223> OTHER INFORMATION: wbeT wild-type CDS insert in reverse
      orientation

<400> SEQUENCE: 13
agtaatacga  ctcactagtg  ggcagatctt  cgaatgcatc  gcgcgcaccg  tacgtctcga      60
ggaattcctg  caggatatct  ggatctatag  tgaactcttc  ggaaatgtct  gttgaacttg     120
caatgacata  cgagaatata  ttaaattatt  ttatgataca  tatttaaaac  agatattccc     180
attaatatcc  tgcgttgctt  tattaaactc  aggatgttca  gcggatgata  atggatgaat     240
aaaatatgcc  ttacttccga  attttgagtt  tattatgtta  aaaatctcat  caaaagttct     300
attagacctc  tgtatatgac  ccattgcaaa  ttcaaagcaa  ataataatatt  caattccatt    360 atgcttttct  gtgaattcgt  aaatctggtt  taatatctct  atttctgcgc  cttcagcatc     420
aatttttata  actacagagt  tagtaggcga  tatatctaaa  ctacttaact  ttctaaccag     480
aacttggcta  tttttaacct  tatctgctat  gtctgtattt  ttttgaaaat  ataatgatga     540
caccctatta  tcaaactcat  aaacttcgaa  atatttttcc  ccttcattct  cacctattgc     600
acagccaaaa  tgatgaaact  caactagtgg  attatttaat  tgaacattca  tcctaatact     660 atttttccatt tctgtgagtg  gttctatcgc  tataatttt  ccttgtgtaa  tatgacgagc     720
agcgattcca  cagaaagttc  caacgtttgc  accgatatca  atataagtgg  tgtcatgctt     780
acaatgatta  acaatccagt  gacgcatacc  taaatcaaag  tttgggtttt  tgtagcttaa     840
agcatggttc  aactgcactc  tgggaaaaca  atgccatcca  aattcgcttt  caagaattaa     900
aaactctcca  ttgtaaatga  agtttcgatt  atcatgaaca  gactttgact  gaatagcatc     960
aagctctgtt  ttaattaatt  tttgtacata  gttttttatt  agatgtttca  tactacctca    1020
attttaaata  atattagcgt  aaaaaataac  atacagaatc  aacttgcaga  tgcagagatc    1080
cacgaagctt  cccatggtga  cgtcaccggt  tctagatacc  taggtgagct  ctggtaccct    1140
```

```
ctagtcaagg cctgtcagcc gttaagtgtt cctgtgtcac tgaaaattgc tttgagaggc       1200
tctaagggct tctcagtgcg ttacatccct ggcttgttgt ccacaaccgt taaaccttaa       1260 aagcttttaaa agccttatat attctttttt ttcttataaa acttaaaacc ttagaggcta      1320
tttaagttgc tgatttatat taattttatt gttcaaacat gagagcttag tacgtgaaac       1380
atgagagctt agtacgttag ccatgagagc ttagtacgtt agccatgagg gtttagttcg       1440
ttaaacatga gagcttagta cgttaaacat gagagcttag tacgtgaaac atgagagctt       1500
agtacgtact atcaacaggt tgaactgctg atcttcagat ctccgcttgc cctcatctgt       1560
tacgccggcg gtagccggcc agcctcgcag agcaggattc ccgttgagca ccgccaggtg       1620
cgaataaggg acagtgaaga aggaacaccc gctcgcgggt gggcctactt cacctatcct       1680
gcccggctga cgccgttgga tacaccaagg aaagtctaca cgaacccttt ggcaaaatcc       1740
tgtatatcgt gcgaaaaagg atggatatac cgaaaaaatc gctaatgac ccccgaagca       1800 gggttatgca gcgaaaagc gctgcttccc tgctgttttg tggaatatct accgactgga       1860
aacaggcaaa tgcaggaaat tactgaactg aggggacagg cgagagatct ggcctaggcc       1920
gaccgaataa atacctgtga cggaagatca cttcgcagaa taaataaatc ctggtgtccc       1980
tgttgatacc gggaagccct gggccaactt ttggcgaaaa tgagacgttg atcggcacgt       2040
aagaggttcc aactttcacc ataatgaaat aagatcacta ccgggcgtat tttttgagtt       2100
gtcgagattt tcaggagcta aggaagctaa atggagaaaa aaatcactg gatataccac         2160 cgttgatata tcccaatggc atcgtaaaga acattttgag gcatttcagt cagttgctca       2220
atgtacctat aaccagaccg ttcagctgga tattacggcc ttttttaaaga ccgtaaagaa      2280 aaataagcac aagttttatc cggcctttat tcacattctt gcccgcctga tgaatgctca       2340
tccggaatta cgtatggcaa tgaaagacgg tgagctggtg atatgggata gtgttcaccc       2400
ttgttacacc gttttccatg agcaaactga aacgttttca tcgctctgga gtgaatacca      2460
cgacgatttc cggcagtttc tacacatata ttcgcaagat gtggcgtgtt acggtgaaaa      2520
cctggcctat ttccctaaag ggtttattga gaatatgttt ttcgtctcag ccaatccctg      2580
ggtgagtttc accagttttg atttaaacgt ggccaatatg gacaacttct tcgcccgtt        2640 ttcaccatgg gcaaatatta tacgcaaggc gacaaggtgc tgatgccgct ggcgattcag       2700
gttcatcatg ccgtttgtga tggcttccat gtcggcagaa tgcttaatga attacaacag       2760
tactgcgatg agtggcaggg cggggcgtaa ttttttttaag gcagttattg gtgcccataa      2820
acgcctggtt gctacgcctg aataagtgat aataagcgga tgaatggcag aaattcgaaa      2880
gcaaattcga cccggtcgtc ggttcagggc agggtcgtta aatagccgct tatgtctatt       2940
gctggtttt                                                              2948
```

<210> SEQ ID NO 14
<211> LENGTH: 24
<212> TYPE: DNA
<213> ORGANISM: Vibrio cholerae

<400> SEQUENCE: 14

```
cggtgcaaac gttggaactt tctg                                               24
```

<210> SEQ ID NO 15
<211> LENGTH: 25
<212> TYPE: DNA
<213> ORGANISM: Vibrio cholerae

<400> SEQUENCE: 15

```
ggaaaacaat gccatccaaa ttcgc                                           25
```

<210> SEQ ID NO 16
<211> LENGTH: 3694
<212> TYPE: DNA
<213> ORGANISM: Artificial
<220> FEATURE:
<223> OTHER INFORMATION: Synthetic construct

<400> SEQUENCE: 16

```
ttcgatattt tttagttctt taggcccgta gtctgcaaat ccttttatga ttttctatca      60
aacaaaagag gaaatagac cagttgcaat ccaaacgaga gtctaataga atgaggtcga     120
aaagtaaatc gcgcgggttt gttactgata aagcaggcaa gacctaaaat gtgtaaaggg    180
caaagtgtat actttggcgt caccccttac atattttagg tcttttttta ttgtgcgtaa    240
ctaacttgcc atcttcaaac aggagggctg gaagaagcag accgctaaca cagtacataa    300
aaaaggagac atgaacgatg aacatcaaaa gtttgcaaa acaagcaaca gtattaacct     360
ttactaccgc actgctggca ggaggcgcaa ctcaagcgtt tgcgaaagaa acgaaccaaa    420
agccatataa ggaaacatac ggcatttccc atattcacg ccatgatatg ctgcaaatcc    480
ctgaacagca aaaaatgaa aaatatcaag ttcctgaatt cgattcgtcc acaattaaaa    540
atatctcttc tgcaaaaggc ctggacgttt gggacagctg gccattacaa aacgctgacg    600
gcactgtcgc aaactatcac ggctaccaca tcgtctttgc attagccgga gatcctaaaa    660
atgcggatga cacatcgatt tacatgttct atcaaaaagt cggcgaaact tctattgaca    720
gctggaaaaa cgctggccgc gtcttaaag acagcgacaa attcgatgca atgattcta    780
tcctaaaaga ccaaacacaa gaatggtcag gttcagccac atttacatct gacggaaaaa    840
tccgtttatt ctacactgat ttctccggta acattacgg caaacaaaca ctgacaactg    900
cacaagttaa cgtatcagca tcagacagct ctttgaacat caacggtgta gaggattata    960
aatcaatctt tgacggtgac ggaaaaacgt atcaaaatgt acagcagttc atcgatgaag   1020
gcaactacag ctcaggcgac aaccatacgc tgagagatcc tcactacgta gaagataaag   1080
gccacaaata cttagtattt gaagcaaaca ctggaactga gatggctac caaggcgaag   1140
aatctttatt taacaaagca tactatggca aaagcacatc attcttccgt caagaaagtc   1200
aaaaacttct gcaaagcgat aaaaaacgca cggctgagtt agcaaacggc gctctcggta   1260
tgattgagct aaacgatgat tacacactga aaaagtgat gaaaccgctg attgcatcta   1320
acacagtaac agatgaaatt gaacgcgcga acgtctttaa aatgaacggc aaatggtacc   1380
tgttcactga ctcccgcgga tcaaaaatga cgattgacgg cattacgtct aacgatattt   1440
acatgcttgg ttatgttct aattctttaa ctggcccata caagccgctg aacaaaactg   1500
gccttgtgtt aaaaatggat cttgatccta acgatgtaac ctttacttac tcacacttcg   1560
ctgtacctca agcgaagga aacaatgtcg tgattacaag ctatatgaca aacagaggat   1620
tctacgcaga caaacaatca acgtttgcgc aagcttcct gctgaacatc aaaggcaaga   1680
aaacatctgt tgtcaaagac agcatccttg aacaaggaca attaacagtt aacaaataaa   1740
aacgcaaaag aaaatgccga ttgaggccag tttgctcagg ctctcccgt ggaggtaata   1800
attgacgata tgatcagtaa tacgactcac tagtgggcag atcttcgaat gcatcgcgcg   1860
caccgtacgt ctcgaggaat tcctgcagga tatctggatc cacgaagctt cccatggtga   1920
cgtcaccggt tctagatacc taggtgagct ctggtaccct ctagtcaagg cctgtcagcc   1980
```

```
gttaagtgtt cctgtgtcac tgaaaattgc tttgagaggc tctaagggct tctcagtgcg    2040
ttacatccct ggcttgttgt ccacaaccgt taaaccttaa aagctttaaa agccttatat    2100 attcttttt ttcttataaa acttaaaacc ttagaggcta tttaagttgc tgatttatat     2160
taattttatt gttcaaacat gagagcttag tacgtgaaac atgagagctt agtacgttag    2220
ccatgagagc ttagtacgtt agccatgagg gtttagttcg ttaaacatga gagcttagta    2280
cgttaaacat gagagcttag tacgtgaaac atgagagctt agtacgtact atcaacaggt    2340
tgaactgctg atcttcagat ctccgcttgc cctcatctgt tacgccggcg gtagccggcc    2400
agcctcgcag agcaggattc ccgttgagca ccgccaggtg cgaataaggg acagtgaaga    2460
aggaacaccc gctcgcgggt gggcctactt caccctatcct gcccggctga cgccgttgga   2520
tacaccaagg aaagtctaca cgaaccctt ggcaaaatcc tgtatatcgt gcgaaaaagg     2580
atggatatac cgaaaaaatc gctataatga ccccgaagca gggttatgca gcggaaaagc    2640
gctgcttccc tgctgttttg tggaatatct accgactgga aacaggcaaa tgcaggaaat    2700
tactgaactg aggggacagg cgagagatct ggcctaggcc gaccgaataa atacctgtga    2760
cggaagatca cttcgcagaa taaataaatc ctggtgtccc tgttgatacc gggaagccct    2820
gggccaactt ttggcgaaaa tgagacgttg atcggcacgt aagaggttcc aactttcacc    2880
ataatgaaat aagatcacta ccgggcgtat tttttgagtt gtcgagattt tcaggagcta    2940
aggaagctaa aatggagaaa aaaatcactg gatataccac cgttgatata tcccaatggc    3000
atcgtaaaga acattttgag gcatttcagt cagttgctca atgtacctat aaccagaccg    3060
ttcagctgga tattacggcc tttttaaaga ccgtaaagaa aaataagcac aagttttatc    3120
cggcctttat tcacattctt gcccgcctga tgaatgctca tccggaatta cgtatggcaa    3180
tgaaagacgg tgagctggtg atatgggata gtgttcaccc ttgttacacc gttttccatg    3240
agcaaactga aacgttttca tcgctctgga gtgaatacca cgacgatttc cggcagtttc    3300
tacacatata ttcgcaagat gtggcgtgtt acggtgaaaa cctggcctat ttccctaaag    3360
ggtttattga gaatatgttt ttcgtctcag ccaatccctg ggtgagtttc accagttttg    3420
atttaaacgt ggccaatatg gacaacttct tcgcccccgt tttcaccatg gcaaatatt     3480 atacgcaagg cgacaaggtg ctgatgccgc tggcgattca ggttcatcat gccgtttgtg    3540
atggcttcca tgtcggcaga atgcttaatg aattacaaca gtactgcgat gagtggcagg    3600
gcggggcgta attttttaa ggcagttatt ggtgcccata aacgcctggt tgctacgcct     3660
gaataagtga taataagcgg atgaatggca gaaa                                3694
```